(12) United States Patent
Beardsley

(10) Patent No.: US 11,324,502 B2
(45) Date of Patent: May 10, 2022

(54) SURGICAL LOADING UNIT INCLUDING AN ARTICULATING END EFFECTOR

(71) Applicant: Covidien LP, Mansfield, MA (US)

(72) Inventor: John Beardsley, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 114 days.

(21) Appl. No.: 16/815,370

(22) Filed: Mar. 11, 2020

(65) Prior Publication Data

US 2020/0205818 A1    Jul. 2, 2020

Related U.S. Application Data

(63) Continuation-in-part of application No. 15/945,404, filed on Apr. 4, 2018, now Pat. No. 10,603,035.

(60) Provisional application No. 62/500,259, filed on May 2, 2017.

(51) Int. Cl.
*A61B 17/072* (2006.01)
*A61B 17/00* (2006.01)

(52) U.S. Cl.
CPC .. *A61B 17/072* (2013.01); *A61B 2017/00398* (2013.01); *A61B 2017/07257* (2013.01); *A61B 2017/07271* (2013.01); *A61B 2017/07285* (2013.01)

(58) Field of Classification Search
CPC .. A61B 2017/2927; A61B 2017/07285; A61B 17/07207; A61B 2017/07214; A61B 17/072
See application file for complete search history.

(56) References Cited

U.S. PATENT DOCUMENTS

| | | | |
|---|---|---|---|
| 2,777,340 A | 1/1957 | Hettwer et al. | |
| 2,957,353 A | 10/1960 | Babacz | |
| 3,079,606 A | 3/1963 | Bobrov et al. | |
| 3,111,328 A | 11/1963 | Di Rito et al. | |
| 3,490,675 A | 1/1970 | Green et al. | |
| 3,499,591 A | 3/1970 | Green | |
| 3,695,058 A | 10/1972 | Keith, Jr. | |
| 3,734,515 A | 5/1973 | Dudek | |
| 3,759,336 A | 9/1973 | Marcovitz et al. | |
| 3,777,538 A | 12/1973 | Weatherly et al. | |

(Continued)

FOREIGN PATENT DOCUMENTS

| AU | 198654765 | 9/1986 |
|---|---|---|
| CA | 2451558 A1 | 1/2003 |

(Continued)

OTHER PUBLICATIONS

Extended European Search Report corresponding to International Application No. EP 14 18 4882.0 dated May 12, 2015.

(Continued)

*Primary Examiner* — Andrew M Tecco
*Assistant Examiner* — Nicholas E Igbokwe

(57) ABSTRACT

A surgical loading unit includes an elongate body, an end effector pivotably coupled to the elongate body, and a flexible knife bar extending through a distal portion of the elongate body and a proximal portion of the end effector. Articulation of the end effector relative to the elongate body in a first direction moves a first segment of the knife bar in the first direction and moves a second segment of the knife bar in a second direction, opposite the first direction.

20 Claims, 10 Drawing Sheets

(56) References Cited

U.S. PATENT DOCUMENTS

| | | |
|---|---|---|
| 3,882,854 A | 5/1975 | Hulka et al. |
| 4,027,510 A | 6/1977 | Hiltebrandt |
| 4,086,926 A | 5/1978 | Green et al. |
| 4,162,399 A | 7/1979 | Hudson |
| 4,241,861 A | 12/1980 | Fleischer |
| 4,244,372 A | 1/1981 | Kapitanov et al. |
| 4,429,695 A | 2/1984 | Green |
| 4,505,414 A | 3/1985 | Filipi |
| 4,520,817 A | 6/1985 | Green |
| 4,589,413 A | 5/1986 | Malyshev et al. |
| 4,596,351 A | 6/1986 | Fedotov et al. |
| 4,602,634 A | 7/1986 | Barkley |
| 4,605,001 A | 8/1986 | Rothfuss et al. |
| 4,606,343 A | 8/1986 | Conta et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,705,038 A | 11/1987 | Sjostrom et al. |
| 4,722,685 A | 2/1988 | de Estrada et al. |
| 4,728,020 A | 3/1988 | Green et al. |
| 4,752,024 A | 6/1988 | Green et al. |
| 4,784,137 A | 11/1988 | Kulik et al. |
| 4,823,807 A | 4/1989 | Russell et al. |
| 4,863,088 A | 9/1989 | Redmond et al. |
| 4,869,415 A | 9/1989 | Fox |
| 4,874,181 A | 10/1989 | Hsu |
| 4,892,244 A | 1/1990 | Fox et al. |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | de Salis et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,118 A | 7/1992 | Walmesley |
| 5,129,570 A | 7/1992 | Schulze et al. |
| 5,141,144 A | 8/1992 | Foslien et al. |
| 5,152,744 A | 10/1992 | Krause et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughett et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,301,061 A | 4/1994 | Nakada et al. |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,350,355 A | 9/1994 | Sklar |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Allen et al. |
| 5,382,255 A | 1/1995 | Castro et al. |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,395,034 A | 3/1995 | Mien et al. |
| 5,397,046 A | 3/1995 | Savage et al. |
| 5,397,324 A | 3/1995 | Carroll et al. |
| 5,400,267 A | 3/1995 | Denen et al. |
| 5,403,312 A | 4/1995 | Yates et al. |
| 5,405,072 A | 4/1995 | Zlock et al. |
| 5,407,293 A | 4/1995 | Crainich |
| 5,411,508 A | 5/1995 | Bessler et al. |
| 5,413,267 A | 5/1995 | Solyntjes et al. |
| 5,413,268 A | 5/1995 | Green et al. |
| 5,415,334 A | 5/1995 | Williamson et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,427,087 A | 6/1995 | Ito et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,445,304 A | 8/1995 | Plyley et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,476,379 A | 12/1995 | Disel |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,490,856 A | 2/1996 | Person et al. |
| 5,497,933 A | 3/1996 | DeFonzo et al. |
| 5,501,689 A | 3/1996 | Green et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,628 A | 8/1996 | Cooper et al. |

(56) References Cited

U.S. PATENT DOCUMENTS

| | | |
|---|---|---|
| 5,549,637 A | 8/1996 | Crainich |
| 5,551,622 A | 9/1996 | Yoon |
| 5,553,675 A | 9/1996 | Pitzen et al. |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,609,560 A | 3/1997 | Ichikawa et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |
| 5,680,982 A | 10/1997 | Schulze et al. |
| 5,680,983 A | 10/1997 | Plyley et al. |
| 5,690,269 A | 11/1997 | Bolanos et al. |
| 5,692,668 A | 12/1997 | Schulze et al. |
| 5,693,042 A | 12/1997 | Boiarski et al. |
| 5,697,542 A | 12/1997 | Knodel et al. |
| 5,702,409 A | 12/1997 | Rayburn et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,715,988 A | 2/1998 | Palmer |
| 5,716,366 A | 2/1998 | Yates |
| 5,718,359 A | 2/1998 | Palmer et al. |
| 5,725,536 A * | 3/1998 | Oberlin ............ A61B 17/07207 606/139 |
| 5,725,554 A | 3/1998 | Simon et al. |
| 5,728,110 A | 3/1998 | Vidal et al. |
| 5,732,806 A | 3/1998 | Foshee et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,762,603 A | 6/1998 | Thompson |
| 5,769,303 A | 6/1998 | Knodel et al. |
| 5,769,892 A | 6/1998 | Kingwell |
| 5,772,099 A | 6/1998 | Gravener |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,785,232 A | 7/1998 | Vidal et al. |
| 5,792,573 A | 8/1998 | Pitzen et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,863,159 A | 1/1999 | Lasko |
| 5,865,361 A | 2/1999 | Milliman et al. |
| 5,871,135 A | 2/1999 | Williamson IV et al. |
| 5,873,873 A | 2/1999 | Smith et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,908,427 A | 6/1999 | McKean et al. |
| 5,911,352 A | 6/1999 | Racenet et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Bittner et al. |
| 5,941,442 A | 8/1999 | Geiste et al. |
| 5,954,259 A | 9/1999 | Viola et al. |
| 5,964,774 A | 10/1999 | McKean et al. |
| 5,980,510 A | 11/1999 | Tsonton et al. |
| 5,988,479 A | 11/1999 | Palmer |
| 5,993,454 A | 11/1999 | Longo |
| 6,004,335 A | 12/1999 | Vaitekunas et al. |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,063,097 A | 5/2000 | Oi et al. |
| 6,079,606 A | 6/2000 | Milliman et al. |
| 6,090,123 A | 7/2000 | Culp et al. |
| 6,099,551 A | 8/2000 | Gabbay |
| 6,109,500 A | 8/2000 | Alli et al. |
| 6,126,651 A | 10/2000 | Mayer |
| 6,129,547 A | 10/2000 | Cise et al. |
| 6,131,789 A | 10/2000 | Schulze et al. |
| 6,131,790 A | 10/2000 | Piraka |
| 6,155,473 A | 12/2000 | Tompkins et al. |
| 6,165,169 A | 12/2000 | Panescu et al. |
| 6,197,017 B1 | 3/2001 | Brock et al. |

(56) References Cited

U.S. PATENT DOCUMENTS

| | | |
|---|---|---|
| 6,202,914 B1 | 3/2001 | Geiste et al. |
| 6,239,732 B1 | 5/2001 | Cusey |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,279,809 B1 | 8/2001 | Nicolo |
| 6,302,311 B1 | 10/2001 | Adams et al. |
| 6,315,183 B1 | 11/2001 | Piraka |
| 6,315,184 B1 | 11/2001 | Whitman |
| 6,321,855 B1 | 11/2001 | Barnes |
| 6,325,810 B1 | 12/2001 | Hamilton et al. |
| 6,329,778 B1 | 12/2001 | Culp et al. |
| 6,330,965 B1 | 12/2001 | Milliman et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,391,038 B2 | 5/2002 | Vargas et al. |
| 6,398,797 B2 | 6/2002 | Bombard et al. |
| 6,434,507 B1 | 8/2002 | Clayton et al. |
| 6,436,097 B1 | 8/2002 | Nardella |
| 6,439,446 B1 | 8/2002 | Perry et al. |
| 6,443,973 B1 | 9/2002 | Whitman |
| 6,461,372 B1 | 10/2002 | Jensen et al. |
| 6,478,804 B2 | 11/2002 | Vargas et al. |
| 6,488,196 B1 | 12/2002 | Fenton, Jr. |
| 6,488,197 B1 | 12/2002 | Whitman |
| 6,491,201 B1 | 12/2002 | Whitman |
| 6,503,257 B2 | 1/2003 | Grant et al. |
| 6,505,768 B2 | 1/2003 | Whitman |
| 6,533,157 B1 | 3/2003 | Whitman |
| 6,537,280 B2 | 3/2003 | Dinger et al. |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,610,066 B2 | 8/2003 | Dinger et al. |
| 6,611,793 B1 | 8/2003 | Burnside et al. |
| 6,619,529 B2 | 9/2003 | Green et al. |
| D480,808 S | 10/2003 | Wells et al. |
| 6,644,532 B2 | 11/2003 | Green et al. |
| 6,645,218 B1 | 11/2003 | Cassidy et al. |
| 6,654,999 B2 | 12/2003 | Stoddard et al. |
| 6,656,193 B2 | 12/2003 | Grant et al. |
| 6,669,073 B2 | 12/2003 | Milliman et al. |
| 6,681,978 B2 | 1/2004 | Geiste et al. |
| 6,698,643 B2 | 3/2004 | Whitman |
| 6,699,177 B1 | 3/2004 | Wang et al. |
| 6,716,232 B1 | 4/2004 | Vidal et al. |
| 6,716,233 B1 | 4/2004 | Whitman |
| 6,722,552 B2 | 4/2004 | Fenton, Jr. |
| 6,743,240 B2 | 6/2004 | Smith et al. |
| 6,755,338 B2 | 6/2004 | Hahnen et al. |
| 6,783,524 B2 | 8/2004 | Anderson et al. |
| 6,783,533 B2 | 8/2004 | Green et al. |
| 6,786,382 B1 | 9/2004 | Hoffman |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| 6,846,308 B2 | 1/2005 | Whitman et al. |
| 6,846,309 B2 | 1/2005 | Whitman et al. |
| 6,849,071 B2 | 2/2005 | Whitman et al. |
| RE38,708 E | 3/2005 | Bolanos et al. |
| 6,860,892 B1 | 3/2005 | Tanaka et al. |
| 6,877,647 B2 | 4/2005 | Green et al. |
| 6,889,116 B2 | 5/2005 | Jinno |
| 6,899,538 B2 | 5/2005 | Matoba |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,798 B2 | 4/2006 | Whitman et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| RE39,152 E | 6/2006 | Aust et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,077,856 B2 | 7/2006 | Whitman |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,122,029 B2 | 10/2006 | Koop et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,021 B1 | 7/2007 | Johnson |
| 7,238,195 B2 | 7/2007 | Viola |
| 7,246,734 B2 | 7/2007 | Shelton, IV |
| 7,252,660 B2 | 8/2007 | Kunz |
| 7,258,262 B2 | 8/2007 | Mastri et al. |
| 7,267,682 B1 | 9/2007 | Bender et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,296,772 B2 | 11/2007 | Wang |
| 7,300,444 B1 | 11/2007 | Nielsen et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |

(56) References Cited

U.S. PATENT DOCUMENTS

| | | |
|---|---|---|
| 7,398,907 B2 | 7/2008 | Racenet et al. |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,549,564 B2 | 6/2009 | Boudreaux |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,093 B2 | 1/2010 | Doll et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,699,835 B2 | 4/2010 | Lee et al. |
| 7,703,653 B2 | 4/2010 | Shah et al. |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,738,971 B2 | 6/2010 | Swayze et al. |
| 7,740,159 B2 | 6/2010 | Shelton, IV et al. |
| 7,740,160 B2 | 6/2010 | Viola |
| 7,743,960 B2 | 6/2010 | Whitman et al. |
| 7,744,628 B2 | 6/2010 | Viola |
| 7,753,245 B2 | 7/2010 | Boudreaux et al. |
| 7,753,248 B2 | 7/2010 | Viola |
| 7,757,924 B2 | 7/2010 | Gerbi et al. |
| 7,757,925 B2 | 7/2010 | Viola et al. |
| 7,758,613 B2 | 7/2010 | Whitman |
| 7,762,445 B2 | 7/2010 | Heinrich et al. |
| 7,766,209 B2 | 8/2010 | Baxter, III et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |
| 7,770,773 B2 | 8/2010 | Whitman et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |
| 7,780,055 B2 | 8/2010 | Scirica et al. |
| 7,784,662 B2 | 8/2010 | Wales et al. |
| 7,789,283 B2 | 9/2010 | Shah |
| 7,789,889 B2 | 9/2010 | Zubik et al. |
| 7,793,812 B2 | 9/2010 | Moore et al. |
| 7,793,814 B2 | 9/2010 | Racenet et al. |
| 7,794,475 B2 | 9/2010 | Hess et al. |
| 7,798,385 B2 | 9/2010 | Boyden et al. |

(56) References Cited

U.S. PATENT DOCUMENTS

| | | |
|---|---|---|
| 7,798,386 B2 | 9/2010 | Schall et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,810,690 B2 | 10/2010 | Bilotti et al. |
| 7,810,692 B2 | 10/2010 | Hall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,896 B2 | 10/2010 | Racenet |
| 7,822,458 B2 | 10/2010 | Webster, III et al. |
| 7,823,760 B2 | 11/2010 | Zemlok et al. |
| 7,823,761 B2 | 11/2010 | Boyden et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,630 B2 | 11/2010 | Damadian et al. |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |
| 7,866,526 B2 | 1/2011 | Green et al. |
| 7,866,527 B2 | 1/2011 | Hall et al. |
| 7,866,528 B2 | 1/2011 | Olson et al. |
| 7,870,989 B2 | 1/2011 | Viola et al. |
| 7,886,952 B2 | 2/2011 | Scirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,905,897 B2 | 3/2011 | Whitman et al. |
| 7,909,039 B2 | 3/2011 | Hur |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,922,061 B2 | 4/2011 | Shelton, IV et al. |
| 7,922,063 B2 | 4/2011 | Zemlok et al. |
| 7,922,064 B2 | 4/2011 | Boyden et al. |
| 7,922,719 B2 | 4/2011 | Ralph et al. |
| 7,926,691 B2 | 4/2011 | Viola et al. |
| 7,926,692 B2 | 4/2011 | Racenet et al. |
| 7,934,628 B2 | 5/2011 | Wenchell et al. |
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,942,303 B2 | 5/2011 | Shah |
| 7,947,034 B2 | 5/2011 | Whitman |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,951,071 B2 | 5/2011 | Whitman et al. |
| 7,954,682 B2 | 6/2011 | Giordano et al. |
| 7,954,683 B1 | 6/2011 | Knodel et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,959,051 B2 | 6/2011 | Smith et al. |
| 7,963,431 B2 | 6/2011 | Scirica |
| 7,963,432 B2 | 6/2011 | Knodel et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,180 B2 | 6/2011 | Scirica |
| 7,975,894 B2 | 7/2011 | Boyden et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,758 B2 | 8/2011 | Whitman et al. |
| 7,997,468 B2 | 8/2011 | Farascioni |
| 7,997,469 B2 | 8/2011 | Olson et al. |
| 8,002,795 B2 | 8/2011 | Beetel |
| 8,006,885 B2 | 8/2011 | Marczyk |
| 8,006,887 B2 | 8/2011 | Marczyk |
| 8,007,505 B2 | 8/2011 | Weller et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,552 B2 | 9/2011 | Ivanko |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,015,976 B2 | 9/2011 | Shah |
| 8,016,177 B2 | 9/2011 | Bettuchi et al. |
| 8,016,178 B2 | 9/2011 | Olson et al. |
| 8,016,855 B2 | 9/2011 | Whitman et al. |
| 8,020,742 B2 | 9/2011 | Marczyk |
| 8,020,743 B2 | 9/2011 | Shelton, IV |
| 8,025,199 B2 | 9/2011 | Whitman et al. |
| 8,028,882 B2 | 10/2011 | Viola |
| 8,028,883 B2 | 10/2011 | Stopek |
| 8,028,884 B2 | 10/2011 | Sniffin et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,035,487 B2 | 10/2011 | Malackowski |
| 8,038,044 B2 | 10/2011 | Viola |
| 8,038,045 B2 | 10/2011 | Bettuchi et al. |
| 8,052,024 B2 | 11/2011 | Viola et al. |
| 8,056,787 B2 | 11/2011 | Boudreaux et al. |
| 8,056,788 B2 | 11/2011 | Mastri et al. |
| 8,056,791 B2 | 11/2011 | Whitman |
| 8,061,577 B2 | 11/2011 | Racenet et al. |
| 8,066,166 B2 | 11/2011 | Demmy et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,074,858 B2 | 12/2011 | Marczyk |
| 8,074,859 B2 | 12/2011 | Kostrzewski |
| 8,074,862 B2 | 12/2011 | Shah |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,091,756 B2 | 1/2012 | Viola |
| 8,092,493 B2 | 1/2012 | Marczyk |
| 8,096,459 B2 | 1/2012 | Ortiz et al. |
| 8,096,460 B2 | 1/2012 | Blier et al. |

(56) References Cited

U.S. PATENT DOCUMENTS

| | | |
|---|---|---|
| 8,100,309 B2 | 1/2012 | Marczyk |
| 8,100,310 B2 | 1/2012 | Zemlok |
| 8,102,008 B2 | 1/2012 | Wells |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,409 B2 | 2/2012 | Cohen et al. |
| 8,113,410 B2 | 2/2012 | Hall et al. |
| 8,114,118 B2 | 2/2012 | Knodel et al. |
| 8,123,101 B2 | 2/2012 | Racenet et al. |
| 8,127,975 B2 | 3/2012 | Olson et al. |
| 8,127,976 B2 | 3/2012 | Scirica et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,136,713 B2 | 3/2012 | Hathaway et al. |
| 8,141,762 B2 | 3/2012 | Bedi et al. |
| 8,152,041 B2 | 4/2012 | Kostrzewski |
| 8,152,516 B2 | 4/2012 | Harvey et al. |
| 8,157,148 B2 | 4/2012 | Scirica |
| 8,157,150 B2 | 4/2012 | Viola et al. |
| 8,157,151 B2 | 4/2012 | Ingmanson et al. |
| 8,157,152 B2 | 4/2012 | Holsten et al. |
| 8,162,197 B2 | 4/2012 | Mastri et al. |
| 8,167,185 B2 | 5/2012 | Shelton, IV et al. |
| 8,167,186 B2 | 5/2012 | Racenet et al. |
| 8,172,121 B2 | 5/2012 | Krehel |
| 8,172,124 B2 | 5/2012 | Shelton, IV et al. |
| 8,181,837 B2 | 5/2012 | Roy |
| 8,182,494 B1 | 5/2012 | Yencho et al. |
| 8,186,555 B2 | 5/2012 | Shelton, IV et al. |
| 8,186,557 B2 | 5/2012 | Cohen et al. |
| 8,186,558 B2 | 5/2012 | Sapienza |
| 8,186,559 B1 | 5/2012 | Whitman |
| 8,186,560 B2 | 5/2012 | Hess et al. |
| 8,186,587 B2 | 5/2012 | Zmood et al. |
| 8,193,044 B2 | 6/2012 | Kenneth |
| 8,196,795 B2 | 6/2012 | Moore et al. |
| 8,196,796 B2 | 6/2012 | Shelton, IV et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,412 B2 | 7/2012 | Marczyk |
| 8,210,416 B2 | 7/2012 | Milliman et al. |
| 8,215,532 B2 | 7/2012 | Marczyk |
| 8,216,236 B2 | 7/2012 | Heinrich et al. |
| 8,220,367 B2 | 7/2012 | Hsu |
| 8,220,688 B2 | 7/2012 | Laurent et al. |
| 8,220,690 B2 | 7/2012 | Hess et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,272 B2 | 8/2012 | Nicholas et al. |
| 8,235,273 B2 | 8/2012 | Olson et al. |
| 8,235,274 B2 | 8/2012 | Cappola |
| 8,236,010 B2 | 8/2012 | Ortiz et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,897 B2 | 8/2012 | Tzakis et al. |
| 8,245,898 B2 | 8/2012 | Smith et al. |
| 8,245,899 B2 | 8/2012 | Swensgard et al. |
| 8,245,931 B2 | 8/2012 | Shigeta |
| 8,252,009 B2 | 8/2012 | Weller et al. |
| 8,256,653 B2 | 9/2012 | Farascioni |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,267,300 B2 | 9/2012 | Boudreaux |
| 8,272,551 B2 | 9/2012 | Knodel et al. |
| 8,272,553 B2 | 9/2012 | Mastri et al. |
| 8,272,554 B2 | 9/2012 | Whitman et al. |
| 8,276,594 B2 | 10/2012 | Shah |
| 8,276,801 B2 | 10/2012 | Zemlok et al. |
| 8,281,973 B2 | 10/2012 | Wenchell et al. |
| 8,286,847 B2 | 10/2012 | Taylor |
| 8,286,848 B2 | 10/2012 | Wenchell et al. |
| 8,286,850 B2 | 10/2012 | Viola |
| 8,292,146 B2 | 10/2012 | Holsten et al. |
| 8,292,147 B2 | 10/2012 | Viola |
| 8,292,148 B2 | 10/2012 | Viola |
| 8,292,149 B2 | 10/2012 | Ivanko |
| 8,292,150 B2 | 10/2012 | Bryant |
| 8,292,151 B2 | 10/2012 | Viola |
| 8,292,152 B2 | 10/2012 | Milliman et al. |
| 8,292,153 B2 | 10/2012 | Jankowski |
| 8,292,154 B2 | 10/2012 | Marczyk |
| 8,292,155 B2 | 10/2012 | Shelton, IV et al. |
| 8,292,156 B2 | 10/2012 | Kostrzewski |
| 8,292,158 B2 | 10/2012 | Sapienza |
| 8,292,888 B2 | 10/2012 | Whitman |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |
| 8,308,044 B2 | 11/2012 | Viola |
| 8,308,046 B2 | 11/2012 | Prommersberger |
| 8,308,757 B2 | 11/2012 | Hillstead et al. |
| 8,317,070 B2 | 11/2012 | Hueil et al. |
| 8,317,071 B1 | 11/2012 | Knodel |
| 8,322,455 B2 | 12/2012 | Shelton, IV et al. |
| 8,322,589 B2 | 12/2012 | Boudreaux |
| 8,328,061 B2 | 12/2012 | Kasvikis |
| 8,328,065 B2 | 12/2012 | Shah |
| 8,333,313 B2 | 12/2012 | Boudreaux et al. |
| 8,336,751 B2 | 12/2012 | Scirica |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,348,855 B2 | 1/2013 | Hillely et al. |
| 8,353,437 B2 | 1/2013 | Boudreaux |
| 8,353,440 B2 | 1/2013 | Whitman et al. |
| 8,356,740 B1 | 1/2013 | Knodel |
| 9,198,644 B2 | 12/2015 | Balek et al. |
| 9,198,661 B2 | 12/2015 | Swensgard |
| 9,204,876 B2 | 12/2015 | Cappola et al. |
| 9,216,013 B2 | 12/2015 | Scirica et al. |
| 9,216,019 B2 | 12/2015 | Schmid et al. |
| 9,216,020 B2 | 12/2015 | Zhang et al. |
| 9,220,500 B2 | 12/2015 | Swayze et al. |
| 9,220,501 B2 | 12/2015 | Baxter, III et al. |
| 9,220,502 B2 | 12/2015 | Zemlok et al. |
| 9,232,941 B2 | 1/2016 | Mandakolathur Vasudevan et al. |
| 9,232,944 B2 | 1/2016 | Cappola et al. |
| 9,237,891 B2 | 1/2016 | Shelton, IV |
| 9,241,712 B2 | 1/2016 | Zemlok et al. |
| 9,254,180 B2 | 2/2016 | Huitema et al. |
| 9,265,585 B2 | 2/2016 | Wingardner et al. |
| 9,271,728 B2 | 3/2016 | Gupta et al. |
| 9,277,919 B2 | 3/2016 | Timmer et al. |
| 9,282,961 B2 | 3/2016 | Whitman et al. |
| 9,282,962 B2 | 3/2016 | Schmid et al. |
| 9,282,963 B2 | 3/2016 | Bryant |
| 9,283,054 B2 | 3/2016 | Morgan et al. |
| 9,289,209 B2 | 3/2016 | Gurumurthy et al. |
| 9,289,210 B2 | 3/2016 | Baxter, III et al. |
| 9,289,225 B2 | 3/2016 | Shelton, IV et al. |
| 9,295,464 B2 | 3/2016 | Shelton, IV et al. |
| 9,295,465 B2 | 3/2016 | Farascioni |
| 9,295,522 B2 | 3/2016 | Kostrzewski |
| 9,301,752 B2 | 4/2016 | Mandakolathur Vasudevan et al. |
| 9,301,753 B2 | 4/2016 | Aldridge et al. |

(56) References Cited

U.S. PATENT DOCUMENTS

| | | |
|---|---|---|
| 9,301,757 B2 | 4/2016 | Williams |
| 9,307,965 B2 | 4/2016 | Ming et al. |
| 9,307,986 B2 | 4/2016 | Hall et al. |
| 9,307,989 B2 | 4/2016 | Shelton, IV et al. |
| 9,314,246 B2 | 4/2016 | Shelton, IV et al. |
| 9,320,518 B2 | 4/2016 | Henderson et al. |
| 9,320,521 B2 | 4/2016 | Shelton, IV et al. |
| 9,326,767 B2 | 5/2016 | Koch, Jr. et al. |
| 9,332,987 B2 | 5/2016 | Leimbach et al. |
| 9,345,477 B2 | 5/2016 | Anim et al. |
| 9,345,478 B2 | 5/2016 | Knodel |
| 9,345,481 B2 | 5/2016 | Hall et al. |
| 9,345,780 B2 | 5/2016 | Manoharan et al. |
| 9,351,727 B2 | 5/2016 | Leimbach et al. |
| 9,351,732 B2 | 5/2016 | Hodgkinson |
| 9,358,003 B2 | 6/2016 | Hall et al. |
| 9,364,217 B2 | 6/2016 | Kostrzewski et al. |
| 9,364,218 B2 | 6/2016 | Scirica |
| 9,364,219 B2 | 6/2016 | Olson et al. |
| 9,364,220 B2 | 6/2016 | Williams |
| 9,364,233 B2 | 6/2016 | Alexander, III et al. |
| 9,370,358 B2 | 6/2016 | Shelton, IV et al. |
| 9,370,362 B2 | 6/2016 | Petty et al. |
| 9,386,983 B2 | 7/2016 | Swensgard et al. |
| 9,386,984 B2 | 7/2016 | Aronhalt et al. |
| 9,386,988 B2 | 7/2016 | Baxter, III et al. |
| 9,393,018 B2 | 7/2016 | Wang et al. |
| 9,398,911 B2 | 7/2016 | Auld |
| 9,402,604 B2 | 8/2016 | Williams et al. |
| 9,421,014 B2 | 8/2016 | Ingmanson et al. |
| 9,433,419 B2 | 9/2016 | Gonzalez et al. |
| 9,433,420 B2 | 9/2016 | Hodgkinson |
| 9,445,810 B2 | 9/2016 | Cappola |
| 9,445,813 B2 | 9/2016 | Shelton, IV et al. |
| 9,451,959 B2 | 9/2016 | Patankar et al. |
| 9,468,438 B2 | 10/2016 | Baber et al. |
| 9,468,439 B2 | 10/2016 | Cappola et al. |
| 9,480,476 B2 | 11/2016 | Aldridge et al. |
| 9,480,492 B2 | 11/2016 | Aranyi et al. |
| 9,492,171 B2 | 11/2016 | Patenaude |
| 9,498,212 B2 | 11/2016 | Racenet et al. |
| 9,510,827 B2 | 12/2016 | Kostrzewski |
| 9,517,065 B2 | 12/2016 | Simms et al. |
| 9,517,066 B2 | 12/2016 | Racenet et al. |
| 9,539,007 B2 | 1/2017 | Dhakad et al. |
| 9,549,735 B2 | 1/2017 | Shelton, IV et al. |
| 10,603,035 B2 | 3/2020 | Beardsley |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0034369 A1 | 2/2004 | Sauer et al. |
| 2004/0094597 A1* | 5/2004 | Whitman ......... A61B 17/07207 227/180.1 |
| 2004/0108357 A1 | 6/2004 | Milliman et al. |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2004/0199180 A1 | 10/2004 | Knodel et al. |
| 2004/0199181 A1 | 10/2004 | Knodel et al. |
| 2004/0243151 A1 | 12/2004 | Demmy et al. |
| 2004/0267310 A1 | 12/2004 | Racenet et al. |
| 2005/0125027 A1 | 6/2005 | Knodel et al. |
| 2005/0131442 A1 | 6/2005 | Yachia et al. |
| 2005/0216055 A1 | 9/2005 | Scirica et al. |
| 2006/0049229 A1 | 3/2006 | Milliman et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0180634 A1 | 8/2006 | Shelton et al. |
| 2006/0190031 A1* | 8/2006 | Wales ............ A61B 17/00234 606/205 |
| 2006/0259073 A1 | 11/2006 | Miyamoto et al. |
| 2006/0278680 A1 | 12/2006 | Viola et al. |
| 2006/0284730 A1 | 12/2006 | Schmid et al. |
| 2006/0289602 A1 | 12/2006 | Wales et al. |
| 2007/0023476 A1 | 2/2007 | Whitman et al. |
| 2007/0023477 A1 | 2/2007 | Whitman et al. |
| 2007/0027469 A1 | 2/2007 | Smith et al. |
| 2007/0029363 A1 | 2/2007 | Popov |
| 2007/0073341 A1 | 3/2007 | Smith et al. |
| 2007/0084897 A1 | 4/2007 | Shelton et al. |
| 2007/0102472 A1 | 5/2007 | Shelton |
| 2007/0106317 A1 | 5/2007 | Shelton et al. |
| 2007/0119901 A1 | 5/2007 | Ehrenfels et al. |
| 2007/0145096 A1 | 6/2007 | Viola et al. |
| 2007/0152014 A1* | 7/2007 | Gillum ............ A61B 17/07207 227/175.1 |
| 2007/0170225 A1 | 7/2007 | Shelton et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0179528 A1 | 8/2007 | Soltz et al. |
| 2007/0194079 A1 | 8/2007 | Hueil et al. |
| 2007/0194082 A1 | 8/2007 | Morgan et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0078802 A1 | 4/2008 | Hess et al. |
| 2008/0105730 A1* | 5/2008 | Racenet .......... A61B 17/07207 227/176.1 |
| 2008/0109012 A1 | 5/2008 | Falco et al. |
| 2008/0110958 A1 | 5/2008 | McKenna et al. |
| 2008/0110961 A1 | 5/2008 | Voegele et al. |
| 2008/0147089 A1 | 6/2008 | Loh et al. |
| 2008/0167736 A1 | 7/2008 | Swayze et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0287987 A1 | 11/2008 | Boyden et al. |
| 2008/0296346 A1 | 12/2008 | Shelton, IV et al. |
| 2008/0308602 A1 | 12/2008 | Timm et al. |
| 2008/0308603 A1 | 12/2008 | Shelton et al. |
| 2009/0001121 A1 | 1/2009 | Hess et al. |
| 2009/0001130 A1 | 1/2009 | Hess et al. |
| 2009/0012533 A1 | 1/2009 | Barbagli et al. |
| 2009/0090763 A1 | 4/2009 | Zemlok et al. |
| 2009/0090766 A1 | 4/2009 | Knodel |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209946 A1 | 8/2009 | Swayze et al. |
| 2009/0209990 A1 | 8/2009 | Yates et al. |
| 2009/0242610 A1 | 10/2009 | Shelton, IV et al. |
| 2009/0254094 A1 | 10/2009 | Knapp et al. |
| 2009/0255974 A1 | 10/2009 | Viola |
| 2009/0299141 A1 | 12/2009 | Downey et al. |
| 2009/0308907 A1 | 12/2009 | Nalagatla et al. |
| 2010/0012703 A1 | 1/2010 | Calabrese et al. |
| 2010/0023022 A1 | 1/2010 | Zeiner et al. |
| 2010/0069942 A1 | 3/2010 | Shelton, IV |
| 2010/0127041 A1 | 5/2010 | Morgan et al. |
| 2010/0133317 A1 | 6/2010 | Shelton, IV et al. |
| 2010/0147921 A1 | 6/2010 | Olson |
| 2010/0147922 A1 | 6/2010 | Olson |
| 2010/0155453 A1 | 6/2010 | Bombard et al. |

(56) References Cited

U.S. PATENT DOCUMENTS

| | | |
|---|---|---|
| 2010/0193566 A1 | 8/2010 | Scheib et al. |
| 2010/0193568 A1 | 8/2010 | Scheib et al. |
| 2010/0211053 A1 | 8/2010 | Ross et al. |
| 2010/0224668 A1 | 9/2010 | Fontayne et al. |
| 2010/0225073 A1 | 9/2010 | Porter et al. |
| 2010/0249802 A1 | 9/2010 | May et al. |
| 2010/0252611 A1 | 10/2010 | Ezzat et al. |
| 2011/0006101 A1 | 1/2011 | Hall et al. |
| 2011/0024477 A1 | 2/2011 | Hall |
| 2011/0024478 A1 | 2/2011 | Shelton, IV |
| 2011/0036891 A1 | 2/2011 | Zemlok et al. |
| 2011/0071508 A1 | 3/2011 | Duval et al. |
| 2011/0077673 A1 | 3/2011 | Grubac et al. |
| 2011/0087276 A1 | 4/2011 | Bedi et al. |
| 2011/0101069 A1 | 5/2011 | Bombard et al. |
| 2011/0114702 A1 | 5/2011 | Farascioni |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0147433 A1 | 6/2011 | Shelton, IV et al. |
| 2011/0155783 A1 | 6/2011 | Rajappa et al. |
| 2011/0155786 A1 | 6/2011 | Shelton, IV |
| 2011/0155787 A1 | 6/2011 | Baxter, III et al. |
| 2011/0163146 A1 | 7/2011 | Ortiz et al. |
| 2011/0163149 A1 | 7/2011 | Viola |
| 2011/0172648 A1 | 7/2011 | Jeong |
| 2011/0174009 A1 | 7/2011 | Iizuka et al. |
| 2011/0174099 A1 | 7/2011 | Ross et al. |
| 2011/0184245 A1 | 7/2011 | Xia et al. |
| 2011/0192881 A1 | 8/2011 | Balbierz et al. |
| 2011/0192882 A1 | 8/2011 | Hess et al. |
| 2011/0192883 A1 | 8/2011 | Whitman et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0278343 A1 | 11/2011 | Knodel et al. |
| 2011/0290854 A1 | 12/2011 | Timm et al. |
| 2011/0290856 A1 | 12/2011 | Shelton, IV et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0016362 A1 | 1/2012 | Heinrich et al. |
| 2012/0053406 A1 | 3/2012 | Conlon et al. |
| 2012/0061446 A1 | 3/2012 | Knodel et al. |
| 2012/0074199 A1 | 3/2012 | Olson et al. |
| 2012/0074200 A1 | 3/2012 | Schmid et al. |
| 2012/0080478 A1 | 4/2012 | Morgan et al. |
| 2012/0080495 A1 | 4/2012 | Holcomb et al. |
| 2012/0080498 A1 | 4/2012 | Shelton, IV et al. |
| 2012/0089131 A1 | 4/2012 | Zemlok et al. |
| 2012/0091183 A1 | 4/2012 | Manoux et al. |
| 2012/0104071 A1 | 5/2012 | Bryant |
| 2012/0116368 A1 | 5/2012 | Viola |
| 2012/0138659 A1 | 6/2012 | Marczyk et al. |
| 2012/0143002 A1 | 6/2012 | Aranyi et al. |
| 2012/0172924 A1 | 7/2012 | Allen, IV |
| 2012/0175399 A1 | 7/2012 | Shelton et al. |
| 2012/0181322 A1 | 7/2012 | Whitman et al. |
| 2012/0187179 A1 | 7/2012 | Gleiman |
| 2012/0193394 A1 | 8/2012 | Holcomb et al. |
| 2012/0193399 A1 | 8/2012 | Holcomb et al. |
| 2012/0199632 A1 | 8/2012 | Spivey et al. |
| 2012/0211542 A1 | 8/2012 | Racenet |
| 2012/0223121 A1 | 9/2012 | Viola et al. |
| 2012/0234895 A1 | 9/2012 | O'Connor et al. |
| 2012/0234897 A1 | 9/2012 | Shelton, IV et al. |
| 2012/0241492 A1 | 9/2012 | Shelton, IV et al. |
| 2012/0241493 A1 | 9/2012 | Baxter, III et al. |
| 2012/0241504 A1 | 9/2012 | Soltz et al. |
| 2012/0245428 A1 | 9/2012 | Smith et al. |
| 2012/0248169 A1 | 10/2012 | Widenhouse et al. |
| 2012/0253329 A1 | 10/2012 | Zemlok et al. |
| 2012/0286021 A1 | 11/2012 | Kostrzewski |
| 2012/0286022 A1 | 11/2012 | Olson et al. |
| 2012/0298722 A1 | 11/2012 | Hess et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0008937 A1 | 1/2013 | Viola |
| 2013/0012983 A1 | 1/2013 | Kleyman |
| 2013/0015231 A1 | 1/2013 | Kostrzewski |
| 2013/0020375 A1 | 1/2013 | Shelton, IV et al. |
| 2013/0020376 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0032626 A1 | 2/2013 | Smith et al. |
| 2013/0037595 A1 | 2/2013 | Gupta et al. |
| 2013/0041406 A1 | 2/2013 | Bear et al. |
| 2013/0068815 A1 | 3/2013 | Bruewer et al. |
| 2013/0068816 A1 | 3/2013 | Mandakolathur Vasudevan et al. |
| 2013/0068818 A1 | 3/2013 | Kasvikis |
| 2013/0075447 A1 | 3/2013 | Weisenburgh, II et al. |
| 2013/0092717 A1 | 4/2013 | Marczyk et al. |
| 2013/0093149 A1 | 4/2013 | Saur et al. |
| 2013/0098964 A1 | 4/2013 | Smith et al. |
| 2013/0098966 A1 | 4/2013 | Kostrzewski et al. |
| 2013/0098970 A1 | 4/2013 | Racenet et al. |
| 2013/0105545 A1 | 5/2013 | Burbank |
| 2013/0105548 A1 | 5/2013 | Hodgkinson et al. |
| 2013/0105552 A1 | 5/2013 | Weir et al. |
| 2013/0105553 A1 | 5/2013 | (Tarinelli) Racenet et al. |
| 2013/0112730 A1 | 5/2013 | Whitman et al. |
| 2013/0119109 A1 | 5/2013 | Farascioni et al. |
| 2013/0146641 A1 | 6/2013 | Shelton, IV et al. |
| 2013/0146642 A1 | 6/2013 | Shelton, IV et al. |
| 2013/0153636 A1 | 6/2013 | Shelton, IV et al. |
| 2013/0153641 A1 | 6/2013 | Shelton, IV et al. |
| 2013/0161374 A1 | 6/2013 | Swayze et al. |
| 2013/0175316 A1 | 7/2013 | Thompson et al. |
| 2013/0181035 A1 | 7/2013 | Milliman |
| 2013/0184704 A1 | 7/2013 | Beardsley et al. |
| 2013/0186929 A1* | 7/2013 | Williams ......... A61B 17/07207 227/175.1 |
| 2013/0193188 A1 | 8/2013 | Shelton, IV et al. |
| 2013/0214025 A1 | 8/2013 | Zemlok et al. |
| 2013/0256380 A1 | 10/2013 | Schmid et al. |
| 2013/0274722 A1 | 10/2013 | Kostrzewski et al. |
| 2013/0277410 A1 | 10/2013 | Fernandez et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334280 A1 | 12/2013 | Krehel et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0014704 A1 | 1/2014 | Onukuri et al. |
| 2014/0014707 A1 | 1/2014 | Onukuri et al. |
| 2014/0021242 A1 | 1/2014 | Hodgkinson et al. |
| 2014/0025046 A1 | 1/2014 | Williams et al. |
| 2014/0048580 A1 | 2/2014 | Merchant et al. |
| 2014/0061280 A1 | 3/2014 | Ingmanson et al. |
| 2014/0076955 A1 | 3/2014 | Lorenz |
| 2014/0110455 A1 | 4/2014 | Ingmanson et al. |
| 2014/0131419 A1 | 5/2014 | Bettuchi |
| 2014/0138423 A1 | 5/2014 | Whitfield et al. |
| 2014/0151431 A1 | 6/2014 | Hodgkinson et al. |
| 2014/0166720 A1 | 6/2014 | Chowaniec et al. |
| 2014/0166721 A1 | 6/2014 | Stevenson et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0175146 A1 | 6/2014 | Knodel |
| 2014/0175150 A1 | 6/2014 | Shelton, IV et al. |
| 2014/0203062 A1 | 7/2014 | Viola |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236174 A1 | 8/2014 | Williams et al. |
| 2014/0239036 A1 | 8/2014 | Zerkle et al. |

(56) References Cited

U.S. PATENT DOCUMENTS

| | | |
|---|---|---|
| 2014/0239037 A1 | 8/2014 | Boudreaux et al. |
| 2014/0239038 A1 | 8/2014 | Leimbach et al. |
| 2014/0239040 A1 | 8/2014 | Fanelli et al. |
| 2014/0239041 A1 | 8/2014 | Zerkle et al. |
| 2014/0239043 A1 | 8/2014 | Simms et al. |
| 2014/0239044 A1 | 8/2014 | Hoffman |
| 2014/0239047 A1 | 8/2014 | Hodgkinson et al. |
| 2014/0246471 A1 | 9/2014 | Jaworek et al. |
| 2014/0246472 A1 | 9/2014 | Kimsey et al. |
| 2014/0246475 A1 | 9/2014 | Hall et al. |
| 2014/0246478 A1 | 9/2014 | Baber et al. |
| 2014/0252062 A1 | 9/2014 | Mozdzierz |
| 2014/0252064 A1 | 9/2014 | Mozdzierz et al. |
| 2014/0252065 A1 | 9/2014 | Hessler et al. |
| 2014/0263539 A1 | 9/2014 | Leimbach et al. |
| 2014/0263540 A1 | 9/2014 | Covach et al. |
| 2014/0263541 A1 | 9/2014 | Leimbach et al. |
| 2014/0263542 A1 | 9/2014 | Leimbach et al. |
| 2014/0263544 A1 | 9/2014 | Ranucci et al. |
| 2014/0263546 A1 | 9/2014 | Aranyi |
| 2014/0263550 A1 | 9/2014 | Aranyi et al. |
| 2014/0263552 A1 | 9/2014 | Hall et al. |
| 2014/0263553 A1 | 9/2014 | Leimbach et al. |
| 2014/0263554 A1 | 9/2014 | Leimbach et al. |
| 2014/0263555 A1 | 9/2014 | Hufnagel et al. |
| 2014/0263557 A1 | 9/2014 | Schaller |
| 2014/0263558 A1 | 9/2014 | Hausen et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263566 A1 | 9/2014 | Williams et al. |
| 2014/0263570 A1 | 9/2014 | Hopkins et al. |
| 2014/0276932 A1 | 9/2014 | Williams et al. |
| 2014/0284371 A1 | 9/2014 | Morgan et al. |
| 2014/0291379 A1 | 10/2014 | Schellin et al. |
| 2014/0291380 A1 | 10/2014 | Meaner et al. |
| 2014/0291383 A1 | 10/2014 | Spivey et al. |
| 2014/0299647 A1 | 10/2014 | Scirica et al. |
| 2014/0303668 A1 | 10/2014 | Nicholas et al. |
| 2014/0309665 A1 | 10/2014 | Parihar et al. |
| 2014/0332578 A1 | 11/2014 | Fernandez et al. |
| 2014/0339286 A1 | 11/2014 | Motooka et al. |
| 2014/0353358 A1 | 12/2014 | Shelton, IV et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0367445 A1 | 12/2014 | Ingmanson et al. |
| 2014/0367446 A1 | 12/2014 | Ingmanson et al. |
| 2014/0373652 A1 | 12/2014 | Zergiebel et al. |
| 2015/0014392 A1 | 1/2015 | Williams et al. |
| 2015/0048143 A1 | 2/2015 | Scheib et al. |
| 2015/0048144 A1 | 2/2015 | Whitman |
| 2015/0053740 A1 | 2/2015 | Shelton, IV |
| 2015/0053742 A1 | 2/2015 | Shelton, IV et al. |
| 2015/0053744 A1 | 2/2015 | Swayze et al. |
| 2015/0060517 A1 | 3/2015 | Williams |
| 2015/0076205 A1 | 3/2015 | Zergiebel |
| 2015/0076211 A1 | 3/2015 | Irka et al. |
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0133996 A1 | 5/2015 | Shelton, IV et al. |
| 2015/0134076 A1 | 5/2015 | Shelton, IV et al. |
| 2015/0150547 A1 | 6/2015 | Ingmanson et al. |
| 2015/0150556 A1 | 6/2015 | McCuen |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0173744 A1 | 6/2015 | Shelton, IV et al. |
| 2015/0173745 A1 | 6/2015 | Baxter, III et al. |
| 2015/0173746 A1 | 6/2015 | Baxter, III et al. |
| 2015/0173747 A1 | 6/2015 | Baxter, III et al. |
| 2015/0173748 A1 | 6/2015 | Marczyk et al. |
| 2015/0173749 A1 | 6/2015 | Shelton, IV et al. |
| 2015/0173750 A1 | 6/2015 | Shelton, IV et al. |
| 2015/0173755 A1* | 6/2015 | Baxter, III ....... A61B 17/07207 227/180.1 |
| 2015/0173756 A1 | 6/2015 | Baxter, III et al. |
| 2015/0173760 A1 | 6/2015 | Shelton, IV et al. |
| 2015/0173761 A1 | 6/2015 | Shelton, IV et al. |
| 2015/0182220 A1 | 7/2015 | Yates et al. |
| 2015/0201931 A1 | 7/2015 | Zergiebel et al. |
| 2015/0209040 A1 | 7/2015 | Whitman et al. |
| 2015/0250474 A1 | 9/2015 | Abbott et al. |
| 2015/0272577 A1 | 10/2015 | Zemlok et al. |
| 2015/0297199 A1 | 10/2015 | Nicholas et al. |
| 2015/0297225 A1 | 10/2015 | Huitema et al. |
| 2015/0303996 A1 | 10/2015 | Calderoni |
| 2015/0316431 A1 | 11/2015 | Collins et al. |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0351765 A1 | 12/2015 | Valentine et al. |
| 2015/0359534 A1 | 12/2015 | Gibbons, Jr. |
| 2015/0366560 A1 | 12/2015 | Chen et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374376 A1 | 12/2015 | Shelton, IV |
| 2015/0374449 A1 | 12/2015 | Chowaniec et al. |
| 2015/0380187 A1 | 12/2015 | Zergiebel et al. |
| 2016/0030040 A1 | 2/2016 | Calderoni et al. |
| 2016/0051259 A1 | 2/2016 | Hopkins et al. |
| 2016/0058443 A1 | 3/2016 | Yates et al. |
| 2016/0066907 A1 | 3/2016 | Cheney et al. |
| 2016/0067074 A1 | 3/2016 | Thompson et al. |
| 2016/0089137 A1 | 3/2016 | Hess et al. |
| 2016/0095585 A1 | 4/2016 | Zergiebel et al. |
| 2016/0095596 A1 | 4/2016 | Scirica et al. |
| 2016/0100835 A1 | 4/2016 | Linder et al. |
| 2016/0106406 A1 | 4/2016 | Cabrera et al. |
| 2016/0113647 A1 | 4/2016 | Hodgkinson |
| 2016/0113648 A1 | 4/2016 | Zergiebel et al. |
| 2016/0113649 A1 | 4/2016 | Zergiebel et al. |
| 2016/0120542 A1 | 5/2016 | Westling et al. |
| 2016/0166249 A1 | 6/2016 | Knodel |
| 2016/0166253 A1 | 6/2016 | Knodel |
| 2016/0174972 A1 | 6/2016 | Shelton, IV |
| 2016/0199064 A1 | 7/2016 | Shelton, IV et al. |
| 2016/0199084 A1 | 7/2016 | Takei |
| 2016/0206315 A1 | 7/2016 | Olson |
| 2016/0206336 A1 | 7/2016 | Frushour |
| 2016/0235494 A1 | 8/2016 | Shelton, IV et al. |
| 2016/0242773 A1 | 8/2016 | Sadowski et al. |
| 2016/0242774 A1 | 8/2016 | Ebner |
| 2016/0242779 A1 | 8/2016 | Aranyi et al. |
| 2016/0249915 A1 | 9/2016 | Beckman et al. |
| 2016/0249916 A1 | 9/2016 | Shelton, IV et al. |
| 2016/0249918 A1 | 9/2016 | Shelton, IV et al. |
| 2016/0249927 A1 | 9/2016 | Beckman et al. |
| 2016/0249929 A1 | 9/2016 | Cappola et al. |
| 2016/0249945 A1 | 9/2016 | Shelton, IV et al. |
| 2016/0256071 A1 | 9/2016 | Shelton, IV et al. |
| 2016/0256152 A1 | 9/2016 | Kostrzewski |
| 2016/0256154 A1 | 9/2016 | Shelton, IV et al. |
| 2016/0256160 A1 | 9/2016 | Shelton, IV et al. |
| 2016/0256161 A1 | 9/2016 | Overmyer et al. |
| 2016/0256162 A1 | 9/2016 | Shelton, IV et al. |
| 2016/0256163 A1 | 9/2016 | Shelton, IV et al. |
| 2016/0256184 A1 | 9/2016 | Shelton, IV et al. |
| 2016/0256185 A1 | 9/2016 | Shelton, IV et al. |
| 2016/0256187 A1 | 9/2016 | Shelton, IV et al. |
| 2016/0262750 A1 | 9/2016 | Hausen et al. |
| 2016/0270783 A1 | 9/2016 | Yigit et al. |
| 2016/0270788 A1 | 9/2016 | Czernik |
| 2016/0278764 A1 | 9/2016 | Shelton, IV et al. |
| 2016/0278765 A1 | 9/2016 | Shelton, IV et al. |
| 2016/0278771 A1 | 9/2016 | Shelton, IV et al. |
| 2016/0278774 A1 | 9/2016 | Shelton, IV et al. |
| 2016/0278775 A1 | 9/2016 | Shelton, IV et al. |

(56) References Cited

U.S. PATENT DOCUMENTS

| | | |
|---|---|---|
| 2016/0278777 A1 | 9/2016 | Shelton, IV et al. |
| 2016/0278848 A1 | 9/2016 | Boudreaux et al. |
| 2016/0287250 A1 | 10/2016 | Shelton, IV et al. |
| 2016/0287251 A1 | 10/2016 | Shelton, IV et al. |
| 2016/0296216 A1 | 10/2016 | Nicholas |
| 2016/0296226 A1 | 10/2016 | Kostrzewski |
| 2016/0302791 A1 | 10/2016 | Schmitt |
| 2016/0310134 A1 | 10/2016 | Contini et al. |
| 2016/0324514 A1 | 11/2016 | Srinivas et al. |
| 2016/0324518 A1 | 11/2016 | Nicholas et al. |
| 2016/0338703 A1 | 11/2016 | Scirica et al. |
| 2016/0345971 A1 | 12/2016 | Bucciaglia et al. |
| 2016/0345973 A1 | 12/2016 | Marczyk et al. |
| 2016/0354176 A1 | 12/2016 | Schmitt |
| 2016/0367248 A1 | 12/2016 | Baxter, III et al. |
| 2016/0374678 A1 | 12/2016 | Becerra et al. |
| 2017/0000483 A1 | 1/2017 | Motai et al. |
| 2017/0020525 A1 | 1/2017 | Shah |
| 2017/0224339 A1* | 8/2017 | Huang .............. A61B 17/07207 |

FOREIGN PATENT DOCUMENTS

| | | |
|---|---|---|
| CA | 2773414 A1 | 11/2012 |
| CA | 2884962 A1 | 11/2015 |
| CN | 1547454 A | 11/2004 |
| CN | 1957854 A | 5/2007 |
| CN | 101495046 A | 7/2009 |
| CN | 102247182 A | 11/2011 |
| DE | 2744824 A1 | 4/1978 |
| DE | 2903159 A1 | 7/1980 |
| DE | 3114135 A1 | 10/1982 |
| DE | 4213426 A1 | 10/1992 |
| DE | 4300307 A1 | 7/1994 |
| DE | 102008053842 A1 | 5/2010 |
| EP | 0041022 A1 | 12/1981 |
| EP | 0136950 A2 | 4/1985 |
| EP | 0140552 A2 | 5/1985 |
| EP | 0156774 A2 | 10/1985 |
| EP | 0213817 A1 | 3/1987 |
| EP | 0216532 A1 | 4/1987 |
| EP | 0220029 A1 | 4/1987 |
| EP | 0273468 A2 | 7/1988 |
| EP | 0324166 A2 | 7/1989 |
| EP | 0324635 A1 | 7/1989 |
| EP | 0324637 A1 | 7/1989 |
| EP | 0324638 A1 | 7/1989 |
| EP | 0365153 A1 | 4/1990 |
| EP | 0369324 A1 | 5/1990 |
| EP | 0373762 A1 | 6/1990 |
| EP | 0380025 A2 | 8/1990 |
| EP | 0399701 A1 | 11/1990 |
| EP | 0449394 A2 | 10/1991 |
| EP | 0484677 A1 | 5/1992 |
| EP | 0489436 A1 | 6/1992 |
| EP | 0503662 A1 | 9/1992 |
| EP | 0514139 A2 | 11/1992 |
| EP | 0536903 A2 | 4/1993 |
| EP | 0537572 A2 | 4/1993 |
| EP | 0539762 A1 | 5/1993 |
| EP | 0545029 A1 | 6/1993 |
| EP | 0552050 A2 | 7/1993 |
| EP | 0552423 A2 | 7/1993 |
| EP | 0579038 A1 | 1/1994 |
| EP | 0589606 A2 | 3/1994 |
| EP | 0591946 A1 | 4/1994 |
| EP | 0592243 A2 | 4/1994 |
| EP | 0593920 A1 | 4/1994 |
| EP | 0598202 A1 | 5/1994 |
| EP | 0598579 A1 | 5/1994 |
| EP | 0600182 A2 | 6/1994 |
| EP | 0621006 A1 | 10/1994 |
| EP | 0621009 A1 | 10/1994 |
| EP | 0656188 A2 | 6/1995 |
| EP | 0666057 A2 | 8/1995 |
| EP | 0705571 A1 | 4/1996 |
| EP | 0760230 A1 | 3/1997 |
| EP | 1563793 A1 | 8/2005 |
| EP | 1769754 A1 | 4/2007 |
| EP | 1952769 A2 | 8/2008 |
| EP | 2090253 A2 | 8/2009 |
| EP | 2090254 A1 | 8/2009 |
| EP | 2316345 A1 | 5/2011 |
| EP | 2583630 A2 | 4/2013 |
| EP | 2586382 A2 | 5/2013 |
| EP | 2617369 A1 | 7/2013 |
| EP | 2668910 A2 | 12/2013 |
| EP | 2907456 A1 | 8/2015 |
| EP | 3034017 A2 | 6/2016 |
| EP | 3037045 A1 | 6/2016 |
| EP | 3106099 A1 | 12/2016 |
| ES | 2333509 A1 | 2/2010 |
| FR | 391239 A | 10/1908 |
| FR | 2542188 A1 | 9/1984 |
| FR | 2660851 A1 | 10/1991 |
| FR | 2681775 A1 | 4/1993 |
| GB | 1352554 A | 5/1974 |
| GB | 1452185 A | 10/1976 |
| GB | 1555455 A | 11/1979 |
| GB | 2048685 A | 12/1980 |
| GB | 2070499 A | 9/1981 |
| GB | 2141066 A | 12/1984 |
| GB | 2165559 A | 4/1986 |
| JP | 51149985 | 12/1976 |
| JP | 2001087272 | 4/2001 |
| JP | 2005125075 A | 5/2005 |
| KR | 20120022521 A | 3/2012 |
| SU | 659146 A1 | 4/1979 |
| SU | 728848 A1 | 4/1980 |
| SU | 980703 A1 | 12/1982 |
| SU | 990220 A1 | 1/1983 |
| WO | 2008302247 | 7/1983 |
| WO | 8910094 A1 | 11/1989 |
| WO | 9210976 A1 | 7/1992 |
| WO | 9308754 A1 | 5/1993 |
| WO | 9314706 A1 | 8/1993 |
| WO | 2004032760 A2 | 4/2004 |
| WO | 2009071070 A2 | 6/2009 |
| WO | 2011108840 A2 | 9/2011 |
| WO | 2012040984 A1 | 4/2012 |
| WO | 20150191887 A1 | 12/2015 |

OTHER PUBLICATIONS

Canadian Office Action corresponding to International Application No. CA 2640399 dated May 7, 2015.
Japanese Office Action corresponding to International Application No. JP 2011-197365 dated Mar. 23, 2015.
Japanese Office Action corresponding to International Application No. JP 2011-084092 dated May 20, 2015.
Japanese Office Action corresponding to International Application No. JP 2014-148482 dated Jun. 2, 2015.
European Search Report corresponding to International Application No. EP 14 18 9358.6 dated Jul. 8, 2015.
Extended European Search Report corresponding to International Application No. EP 14 19 6148.2 dated Apr. 23, 2015.
Partial European Search Report corresponding to International Application No. EP 14 19 6704.2 dated May 11, 2015.
Australian Office Action corresponding to International Application No. AU 2010241367 dated Aug. 20, 2015.
Partial European Search Report corresponding to International Application No. EP 14 19 9783.3 dated Sep. 3, 2015.
Extended European Search Report corresponding to International Application No. EP 15 16 9962.6 dated Sep. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.

(56) References Cited

OTHER PUBLICATIONS

European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action corresponding to counterpart Int'l Appln. No. CN 201310369318.2 dated Jun. 28, 2016.
Chinese Office Action (with English translation), dated Jul. 4, 2016, corresponding to Chinese Patent Application No. 2015101559718; 23 total pages.
European Search Report EP 15 156 035.6 dated Aug. 10, 2016.
European Search Report corresponding to EP 15 184 915.5-1654 dated Sep. 16, 2016.
Australian Examination Report No. 1 corresponding to International Application No. AU 2013205872 dated Oct. 19, 2016.
Australian Examination Report from Appl. No. AU 2013205840 dated Nov. 3, 2016.
European Search Report, dated Sep. 11, 2018, corresponding to European Application No. 18170242.4; 8 pages.

\* cited by examiner

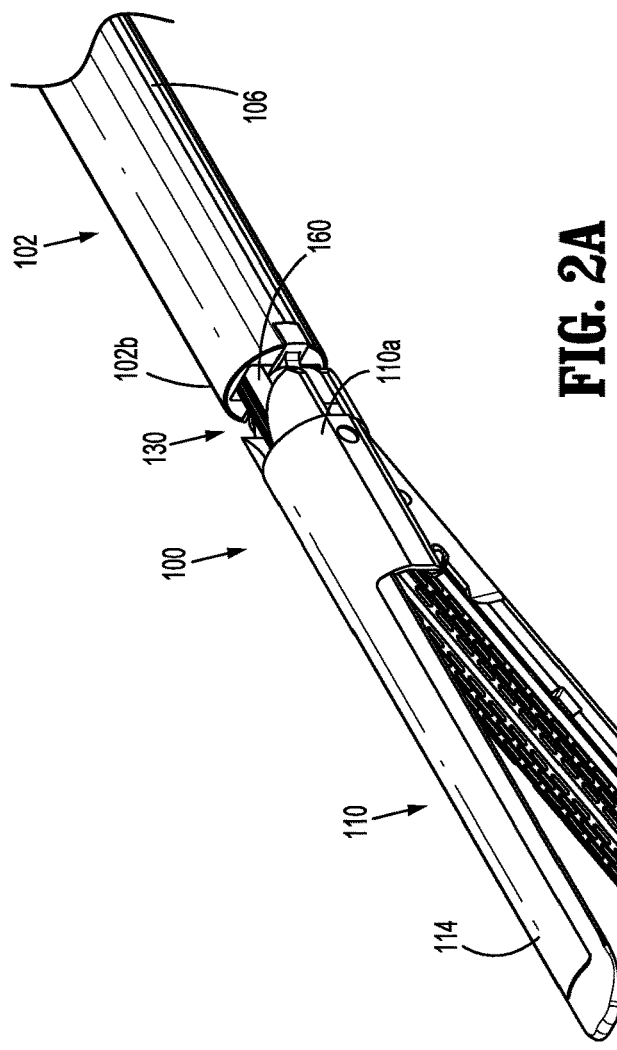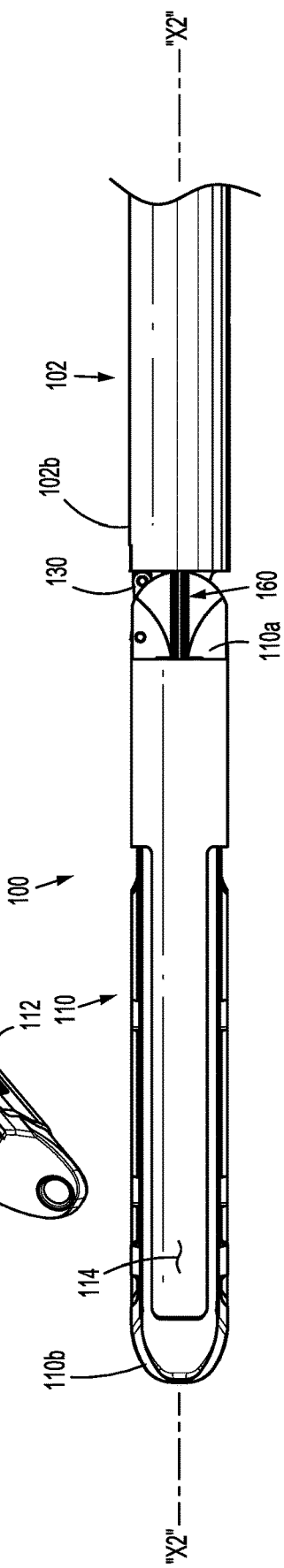
FIG. 2A
FIG. 2B

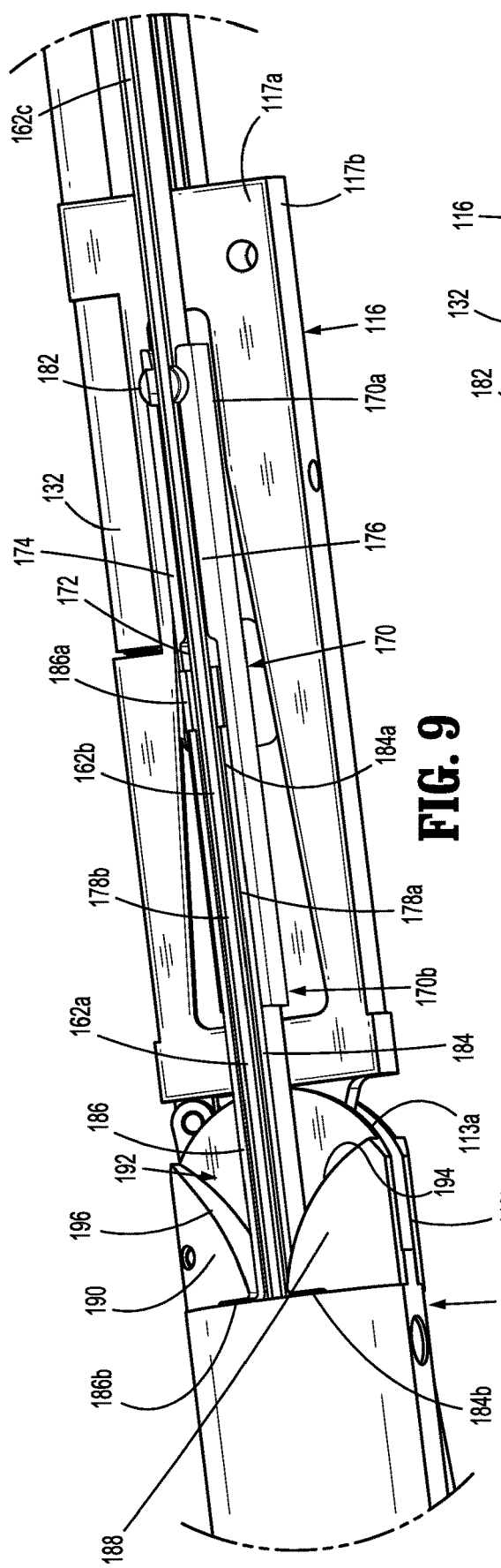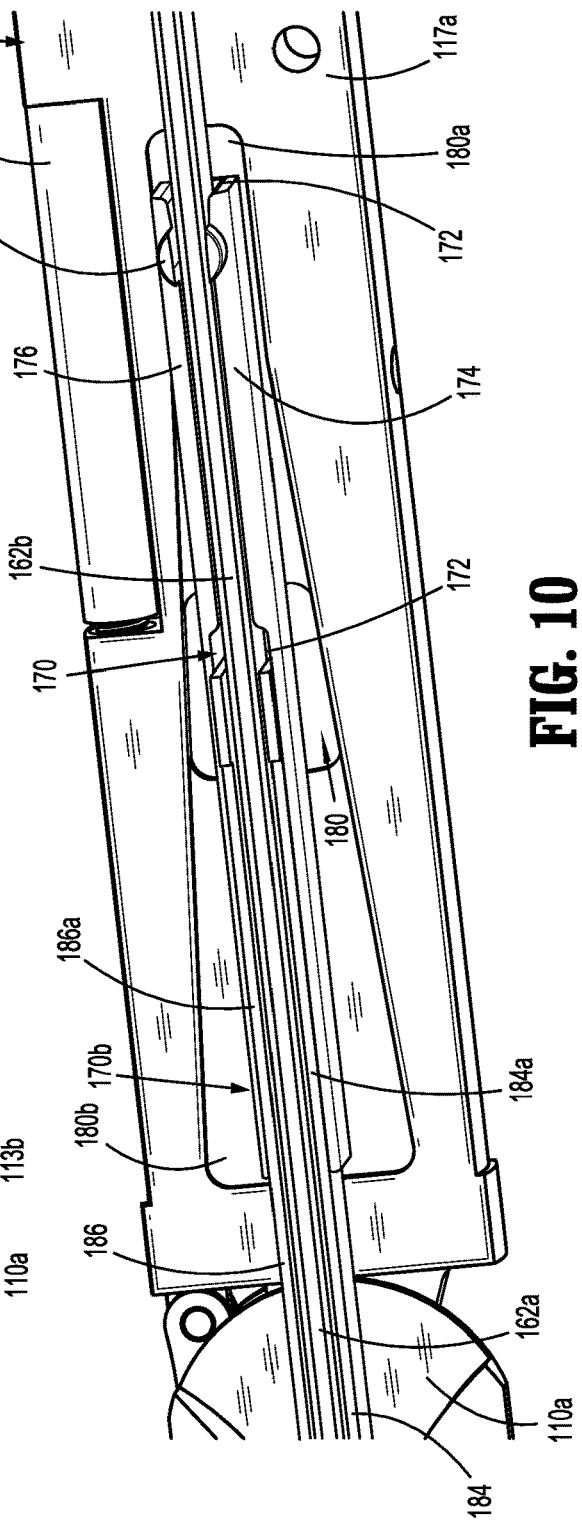

SURGICAL LOADING UNIT INCLUDING AN ARTICULATING END EFFECTOR

CROSS-REFERENCE TO RELATED APPLICATION

This application is a continuation application of U.S. patent application Ser. No. 15/945,404, filed on Apr. 4, 2018, which claims the benefit of and priority to U.S. Provisional Application No. 62/500,259, filed on May 2, 2017, the entire contents of each of which are incorporated by reference herein.

BACKGROUND

Technical Field

The present disclosure relates generally to surgical loading units for endoscopic use and, more specifically, to surgical loading units having articulation assemblies for articulating an end effector of the surgical loading unit.

Background of Related Art

Various types of surgical instruments used to endoscopically treat tissue are known in the art, and are commonly used, for example, for closure of tissue or organs in transection, resection, anastomoses, for occlusion of organs in thoracic and abdominal procedures, and for electrosurgically fusing or sealing tissue.

One example of such a surgical instrument is a surgical stapling instrument. Typically, surgical stapling instruments include an end effector having an anvil assembly and a cartridge assembly for supporting an array of surgical staples, an approximation mechanism for approximating the cartridge and anvil assemblies, and a firing mechanism for ejecting the surgical staples from the cartridge assembly.

During laparoscopic or endoscopic surgical procedures, access to a surgical site is achieved through a small incision or through a narrow cannula inserted through a small entrance wound in a patient. Because of limited area available to access the surgical site, many endoscopic instruments include mechanisms for articulating the end effector of the instrument in relation to a body portion of the instrument to improve access to tissue to be treated. In addition, some end effectors have a knife blade that translates therethrough to tissue grasped by jaws of the end effector. During articulation of the end effector, the knife blade experiences a bending moment and/or a shear force that may degrade the knife blade over continued articulation of the end effector.

Accordingly, it would be beneficial to provide an improved surgical instrument, which includes a mechanism for articulating the end effector relative to the body portion in a variety of orientations without damaging a knife blade that moves through the end effector.

SUMMARY

In one aspect of the present disclosure, a surgical loading unit is provided that includes an elongate body, an end effector having a proximal portion pivotably coupled to a distal portion of the elongate body, and a knife assembly disposed within the elongate body. The knife assembly includes an elongate guide member and a flexible knife bar. The elongate guide member is pivotably supported in the distal portion of the elongate body. The knife bar is configured to move through a longitudinally-extending channel defined through the elongate guide member. Articulation of the end effector relative to the elongate body in a first direction effects movement of a distal portion of the elongate guide member in a second direction, opposite the first direction.

In some embodiments, the elongate body may define a first longitudinal axis and the end effector may define a second longitudinal axis. The end effector may be configured to move relative to the elongate body from a first position in which the second longitudinal axis is aligned with the first longitudinal axis to a second position in which the second longitudinal axis is misaligned with the first longitudinal axis. Upon the end effector moving to the second position, a distal portion of the end effector may be disposed on a first side of a central longitudinal axis defined by the elongate body and the distal portion of the elongate guide member of the knife assembly may be disposed on a second side of the central longitudinal axis defined by the elongate body.

It is contemplated that the knife bar may be more flexible than the elongate guide member such that the elongate guide member is configured to maintain a linear shape as a segment of the knife bar that is located distally of the elongate guide member flexes during articulation of the end effector.

It is envisioned that the knife assembly may further include a pair of blow-out plates extending along opposite sides of the knife bar. The pair of blow-out plates may have a distal portion coupled to the proximal portion of the end effector. A first blow-out plate may have a proximal portion disposed between a first lateral side of the knife bar and a first lateral side of the elongate guide member, and a second blow-out plate may have a proximal portion disposed between a second lateral side of the knife bar and a second lateral side of the elongate guide member. The proximal portion of the first blow-out plate may be configured to slide relative to the elongate guide member in a first axial direction, and the proximal portion of the second blow-out plate may be configured to slide relative to the elongate guide member in a second axial direction in response to the end effector articulating.

In some embodiments, the proximal portion of the end effector may include first and second walls that taper proximally such that the first and second walls cooperatively define a proximally-flaring cavity through which both the distal portion of the knife bar and the pair of blow-out plates extend. Each of the first and second walls may define arcuate side surfaces that are laterally spaced from one another. The arcuate side surface of the first wall may be configured to contact the first blow-out plate when the end effector articulates in the first direction, and the arcuate side surface of the second wall may be configured to contact the second blow-out plate when the end effector articulates in the second direction.

It is contemplated that a proximal portion of the first wall may be configured to contact the first blow-out plate in response to an articulation of the end effector in the first direction to move the distal portion of the elongate guide member in the second direction. The proximal portion of the second wall may be configured to contact the second blow-out plate in response to an articulation of the end effector in the second direction to move the distal portion of the elongate guide member in the first direction.

It is envisioned that a proximal portion of the first wall may be configured to move the distal portion of the elongate guide member in the second direction in response to an articulation of the end effector in the first direction, and a proximal portion of the second wall may be configured to move the distal portion of the elongate guide member in the first direction in response to an articulation of the end effector in the second direction.

In some embodiments, the elongate guide member may include a proximal portion pivotably coupled to the elongate body. The proximal portion of the elongate guide member may have a circular tab pivotably coupled to the elongate body, such that the elongate guide member is prevented from translating longitudinally relative to the elongate body.

It is contemplated that the knife assembly may further include a track defining a longitudinally-extending channel. The flexible knife bar may include a first knife bar shaft and a second knife bar shaft coupled to and extending parallel with the first knife bar shaft. The first knife bar shaft may extend through the channel of the elongate guide member. The second knife bar shaft may extend through the channel of the track.

It is envisioned that the track and the elongate guide member may be less flexible than the knife bar, such that the track and the elongate guide member are configured to maintain a linear shape during articulation of the end effector relative to the elongate body.

In some embodiments, the surgical loading unit may further include a support structure disposed between the first and second knife bar shafts of the flexible knife bar. The support structure may include a top surface on which the elongate guide member is supported, and a bottom surface on which the track is supported.

In some aspects, the elongate body may include a support structure on which the knife assembly is supported. The support structure may have a distal portion pivotably coupled to the proximal portion of the end effector. The support structure may have a planar top surface that defines a distally-flaring cavity therein. The elongate guide member may be disposed within the distally-flaring cavity.

It is contemplated that the elongate body may include an articulation assembly for effecting articulation of the end effector. The articulation assembly may include an elongated drive nut extending through a proximal portion of the support structure, an elongated drive screw extending through a distal portion of the support structure and having a proximal portion threadingly coupled to the drive nut, and an articulation link having a proximal portion pivotably coupled to a distal portion of the drive screw, and a distal portion pivotably coupled to the proximal portion of the end effector. Rotation of the drive nut may axially move the drive screw to pivot the articulation link and, in turn, articulate the end effector.

It is envisioned that the articulation assembly may be laterally offset from a central longitudinal axis defined by the elongate body.

In some embodiments, the knife bar may have a proximal portion operably coupled to an actuator for axially moving the knife bar through the elongate body, and a distal portion that supports a knife blade for cutting tissue. The end effector may include a staple cartridge and an anvil. The staple cartridge may define a longitudinally-extending channel dimensioned for slidable receipt of the knife blade.

In another aspect of the present disclosure, a surgical loading unit is provided that includes an elongate body, an end effector having a proximal portion pivotably coupled to a distal portion of the elongate body, and a flexible knife bar extending through the distal portion of the elongate body and the proximal portion of the end effector. Articulation of the end effector relative to the elongate body in a first direction may curve a first segment of the knife bar in the first direction and may pivot a second segment of the knife bar in a second direction, opposite the first direction, while the second segment maintains a linear shape. The second segment may be disposed proximally of the first segment.

BRIEF DESCRIPTION OF THE DRAWINGS

Surgical loading units including embodiments of the presently disclosed articulation mechanism are disclosed herein with reference to the drawings, wherein:

FIG. 2A is a perspective view of a distal end portion of a surgical loading unit for use with the surgical stapling instruments of FIGS. 1A and 1B;

FIG. 2B is a top view of the loading unit of FIG. 2A;

FIG. 9 is an enlarged view of the indicated area of detail of FIG. 8;

FIG. 10 is an enlarged view of a knife bar, blow-out plates, and a knife bar track of the knife assembly of FIG. 9;

DETAILED DESCRIPTION

Persons skilled in the art will understand that the loading units and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the described embodiments. Accordingly, the disclosure is not to be limited by what has been particularly shown and described, except as indicated by the appended claims.

As used herein, the term "distal" refers to that portion of the surgical instrument or loading unit which is farthest from a clinician, while the term "proximal" refers to that portion of the surgical instrument or loading unit which is closest to the clinician. In addition, as used herein, the term clinician refers to medical staff including doctors, nurses and support personnel.

The present disclosure is directed to a knife assembly for use in an articulating surgical loading unit or surgical instrument. The knife assembly includes a flexible knife bar supported on either side by a knife bar guide. The knife assembly is configured such that upon articulation of an end effector of the loading unit relative to an elongate body of the loading unit, the knife bar of the knife assembly bends in the direction of articulation while also shifting in a direction away from the direction of articulation. The knife bar shifting or pivoting in a substantially opposite direction from which the knife bar is being bent causes the knife bar to assume a larger radius of curvature during articulation of the end effector. Bending along a larger radius of curvature prolongs the life of the knife bar by reducing shear forces and/or bending moments experienced by the knife bar while also providing a greater articulation angle of the end effector.

The present disclosure further provides an articulation assembly for articulating an end effector of a loading unit relative to an elongate body of the loading unit. The articulation assembly includes an elongate drive unit and an elongate drive screw operably coupled to one another and each being disposed toward a distal end of the elongate body, as will described in further detail below.

Additional advantages of the presently disclosed knife assembly, articulation assembly, and surgical loading units including the presently disclosed knife assembly and articulation assembly are described below.

Figure 1A:
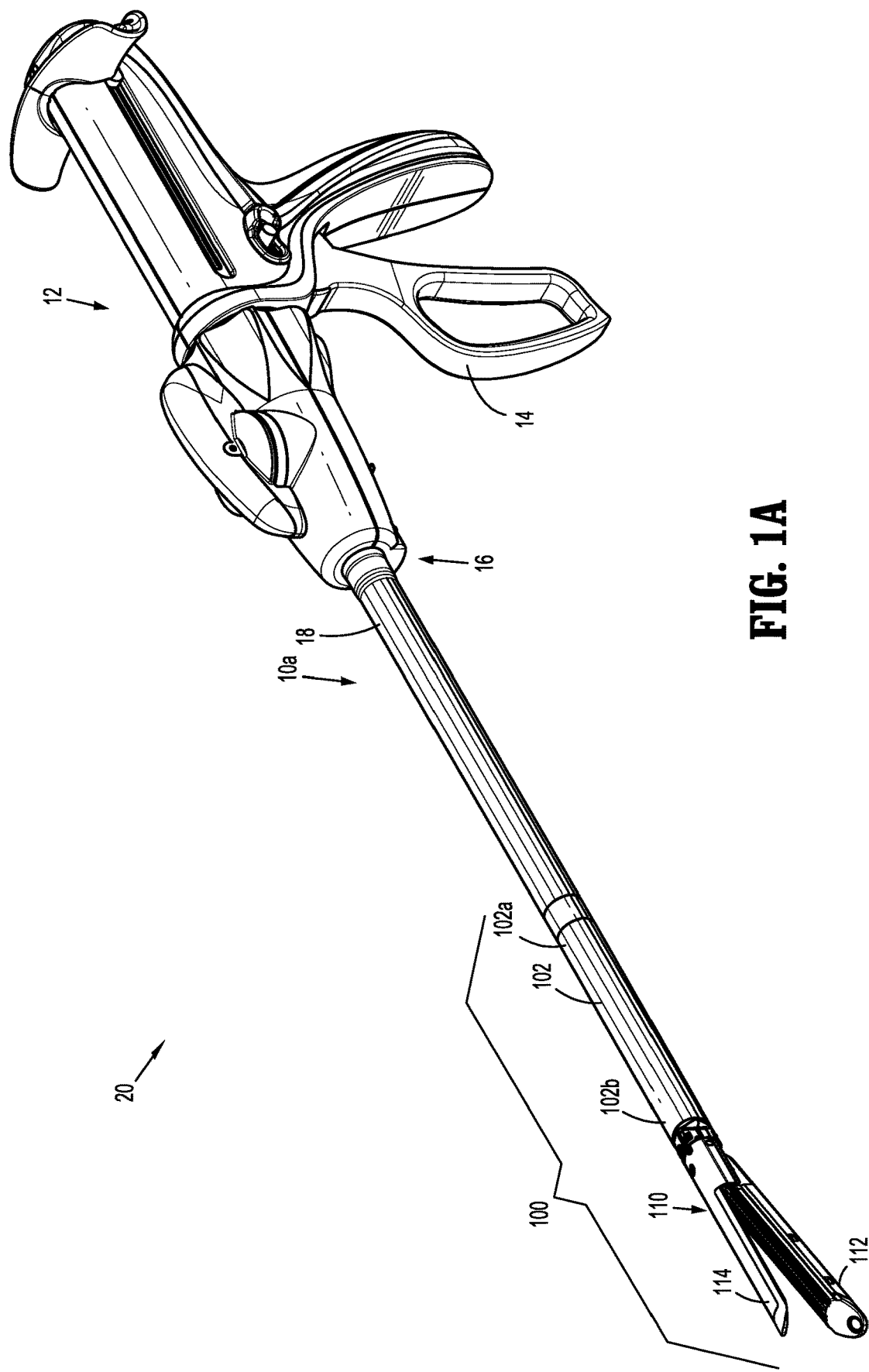
FIG. 1A is a perspective view of a surgical stapling instrument in accordance with the present disclosure.
Figure 1B:
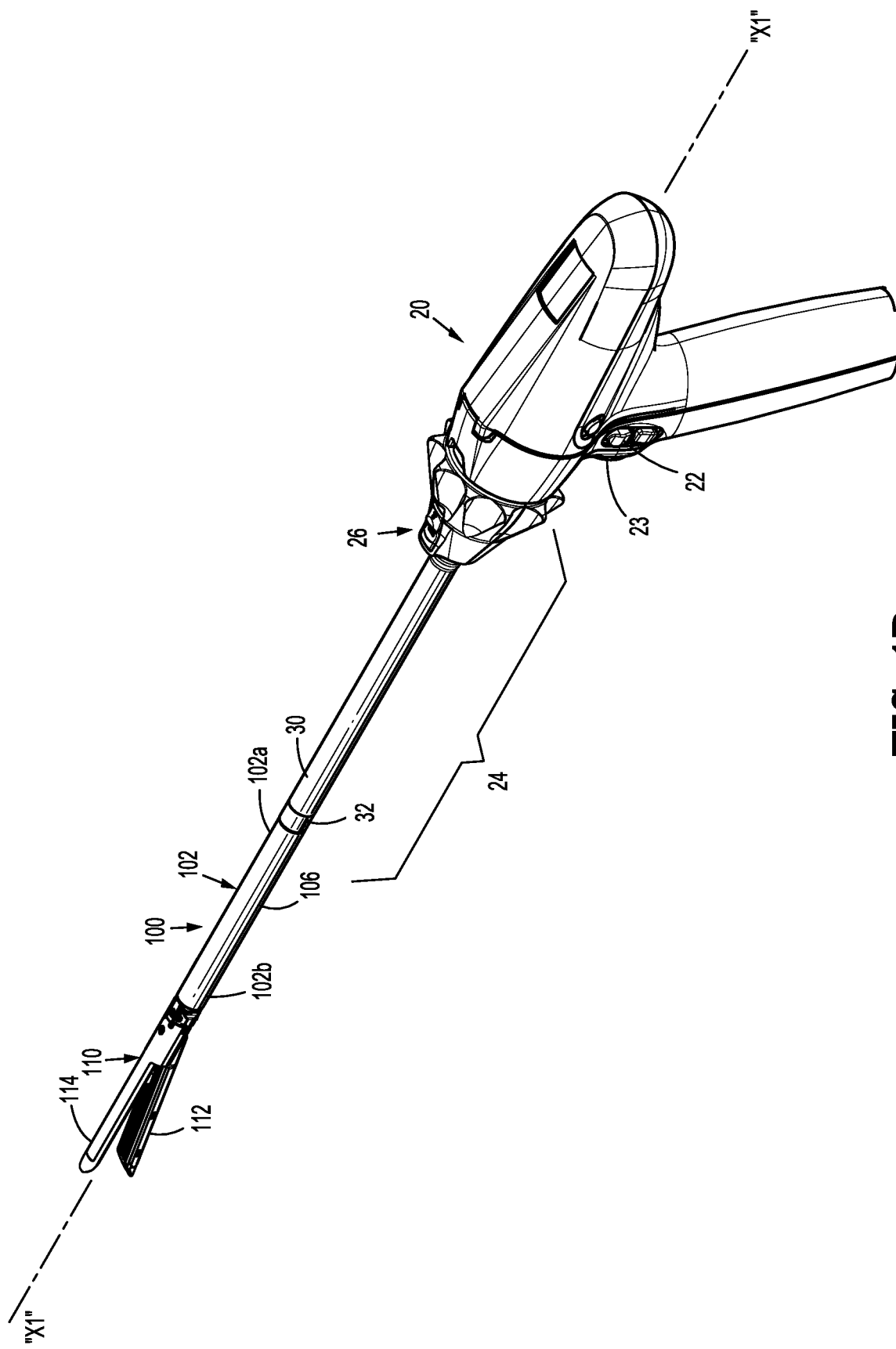
FIG. 1B is a perspective view of another surgical stapling instrument in accordance with the present disclosure, shown in a non-articulated or linear position.

FIGS. 1A and 1B illustrate surgical stapling instruments for use with surgical loading units incorporating embodiments of the presently disclosed articulation assembly 130 and knife assembly 160, referenced generally as surgical stapling instruments 10a and 10b. Each of the surgical stapling instruments 10a and 10b can be used with the same surgical loading unit 100. While the depicted surgical stapling instruments 10a, 10b fire staples, it is contemplated that the surgical loading unit 100 may be adapted to fire any other suitable fastener such as clips and two-part fasteners. Additionally, while the figures depict a linear surgical stapling instrument, it is envisioned that the presently disclosed articulation assembly and knife assembly are suitable for use with other types of endoscopic surgical instruments including non-linear surgical stapler loading units, endoscopic forceps, graspers, dissectors, other types of surgical stapling instruments, powered vessel sealing and/or cutting devices, etc.

Generally, with reference to FIG. 1A, the surgical instrument 10a includes a handle assembly 12 including a movable handle 14, an adapter assembly 16 extending from the handle assembly 12, and a surgical loading unit 100 coupled to a distal end portion of an outer tube 18 of the adapter assembly 16. As known in the art, the movable handle 14 is actuatable (e.g., through one or more strokes) to cause distal advancement of a drive rod (not shown), such that the drive rod engages a portion of a drive assembly (not shown), which forces at least a portion of the drive assembly to translate distally, thereby firing staples from the surgical loading unit 100. Further details of how actuation of the movable handle 14 causes distal advancement of the drive rod are explained in U.S. Pat. No. 6,953,139 to Milliman et al., the entire contents of which are incorporated by reference herein.

Generally, with reference to FIG. 1B, the surgical instrument 10b is a motor-driven electromechanical device that includes a handle assembly 20 including a control or button 22, an adapter assembly 24 coupled to the handle assembly 20, and the surgical loading unit 100 disposed adjacent a distal portion 32 of an outer tube 30 of the adapter assembly 24. The adapter assembly 24 includes an outer knob housing 26 coupled to a distal end portion of the handle assembly 20, and the outer tube 30 of the adapter assembly 24 extends from a distal end portion of the knob housing 26. The button 22 of the handle assembly 20 is in electrical communication with a motorized drive shaft (not shown), which is operatively coupled to an articulation assembly 130 of the loading unit 100 such that actuation of the actuation button 22 causes the articulation mechanism 130 to articulate an end effector 110 of the loading unit 100, as will be described in further detail below.

A detailed description of the various components of the handle assembly 20 and the adapter assembly 24 of surgical instrument 10b may be found, for example, in U.S. patent application Ser. No. 14/550,071 (now U.S. Patent Application Publication No. 2015/0157320), the entire contents of which being incorporated by reference herein.

The loading unit 100 is adapted to be attached to the outer tube 30 of the adapter assembly 24 of the surgical stapling instrument 10b (or the outer tube 18 of the adapter assembly 16 of surgical stapling instrument 10a). The loading unit 100 may be configured for a single use, or may be configured to be used more than once and includes an elongate body 102 and an end effector 110 supported on a distal portion 102b of the elongate body 102. In some embodiments, the end effector 110, including a staple cartridge 112 and an anvil 114, may not form part of the loading unit 100, but rather, may be directly pivotably coupled to the distal portion 32 of the outer tube 30 of the adapter assembly 24.

Figure 2C:
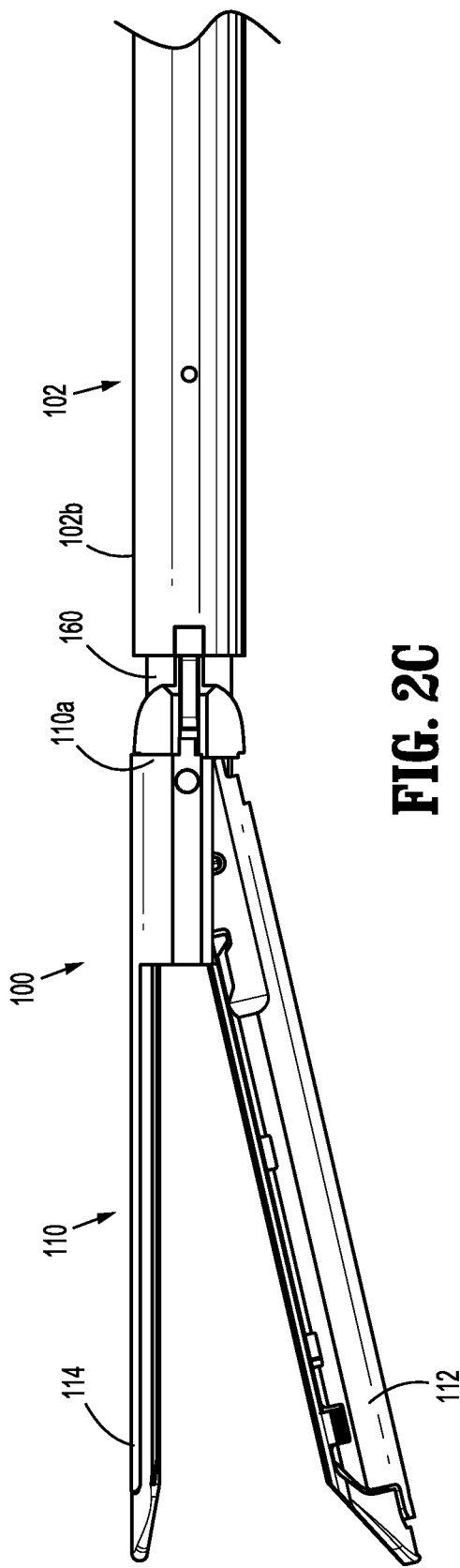
FIG. 2C is a first side view of the loading unit of FIG. 2A.
Figure 2D:
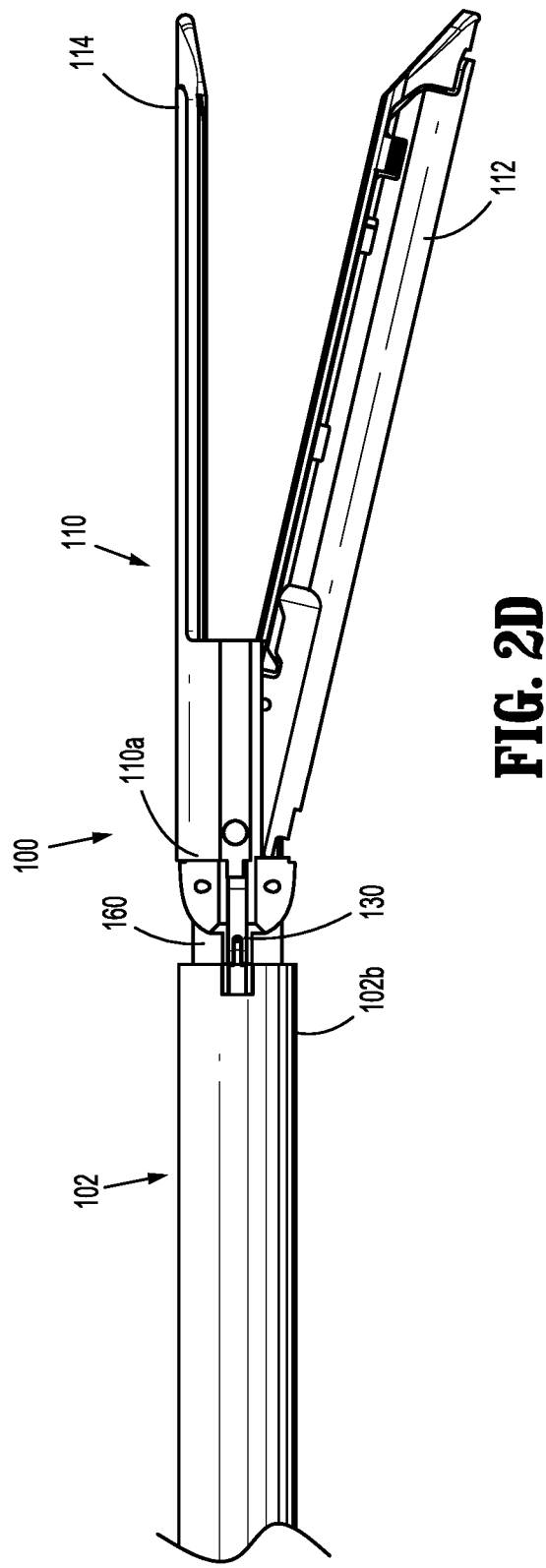
FIG. 2D is a second side view of the loading unit of FIG. 2A.

The elongate body 102 of the loading unit 100 defines a first longitudinal axis "X1" and has a proximal portion 102a removably received within the distal portion 32 of the outer tube 30 of the adapter assembly 24 of the surgical stapling instrument 10b using, e.g., a bayonet or luer type coupling. The elongate body 102 of the loading unit 100 may include an outer housing or tube 106 (FIG. 2A) and an inner housing or tube 108 disposed within the outer housing 106. In some embodiments, the elongate body 102 of the loading unit 100 may be integrally connected to or monolithically formed with the outer tube 30 of the adapter assembly 24 of the surgical stapling instrument 10b.

Figure 6A:
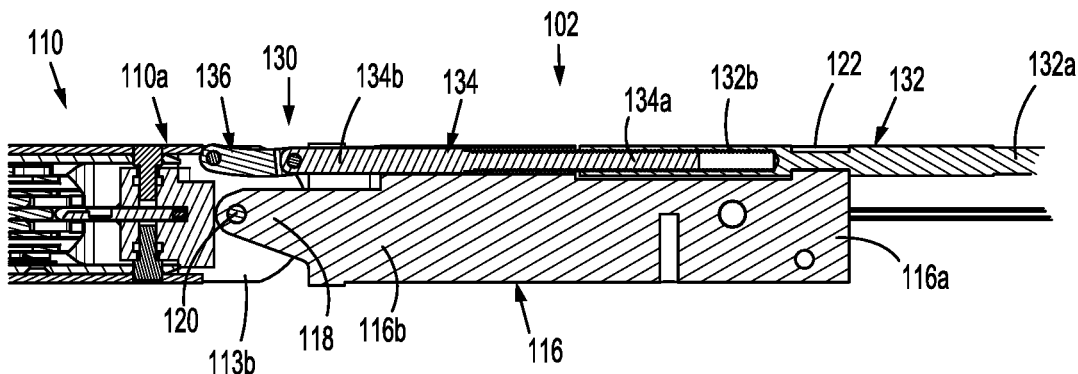
FIG. 6A is a top view of the cross-section of FIG. 5 illustrating the loading unit in a non-articulated position, with an end effector of the loading unit axially aligned with an elongate body of the loading unit.
Figure 6B:
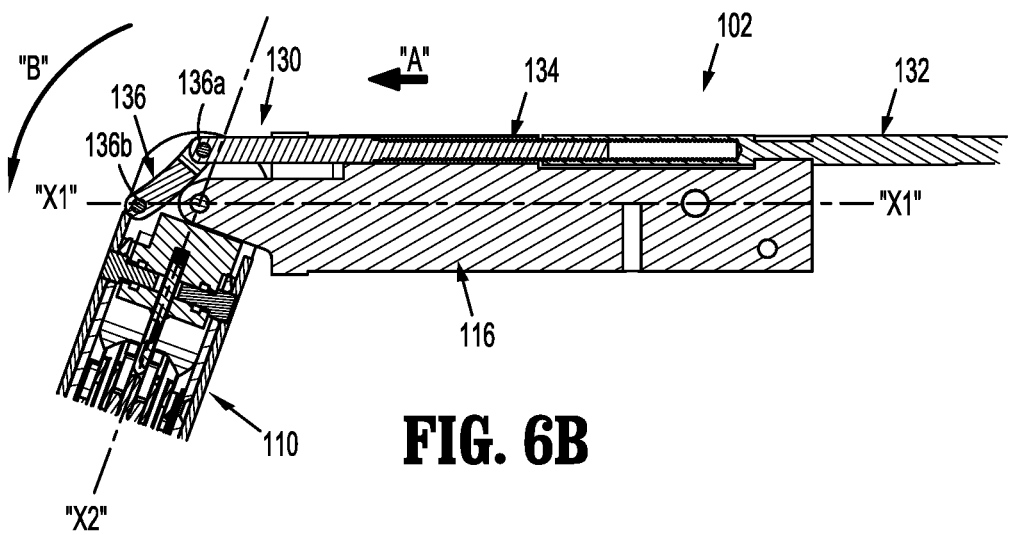
FIG. 6B is a top view of the cross-section of FIG. 5 illustrating the end effector of the loading unit in a first articulated position relative to the elongate body of the loading unit.
Figure 6C:
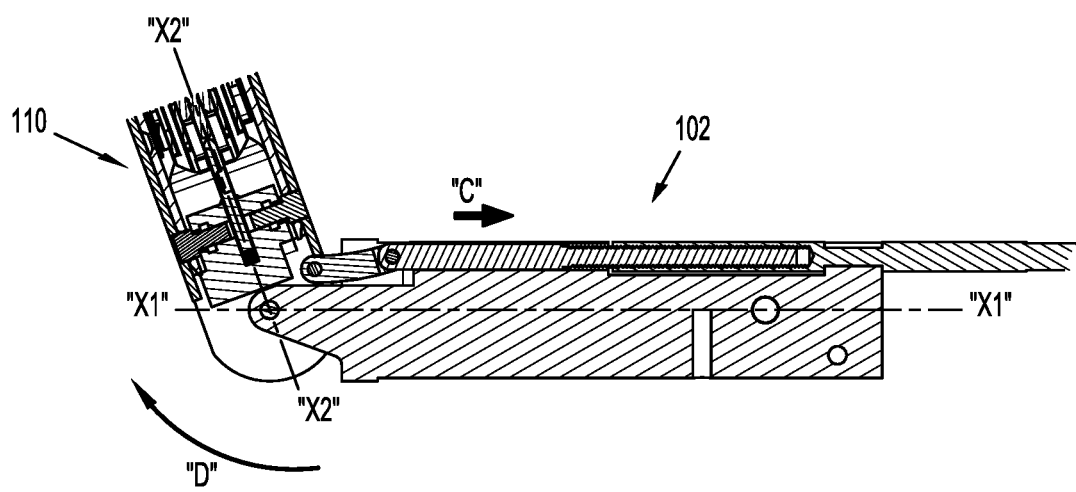
FIG. 6C is a top view of the cross-section of FIG. 5 illustrating the end effector of the loading unit in a second articulated position relative to the elongate body of the loading unit.
Figure 7:
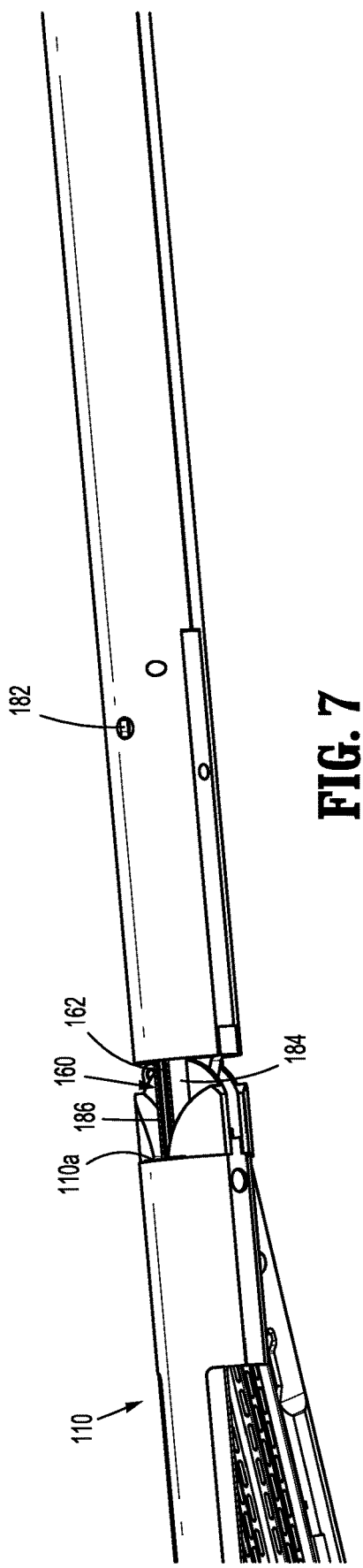
FIG. 7 is a perspective view, with the outer housing of the elongate body removed, of the surgical loading unit illustrating the knife assembly of the loading unit.
Figure 8:
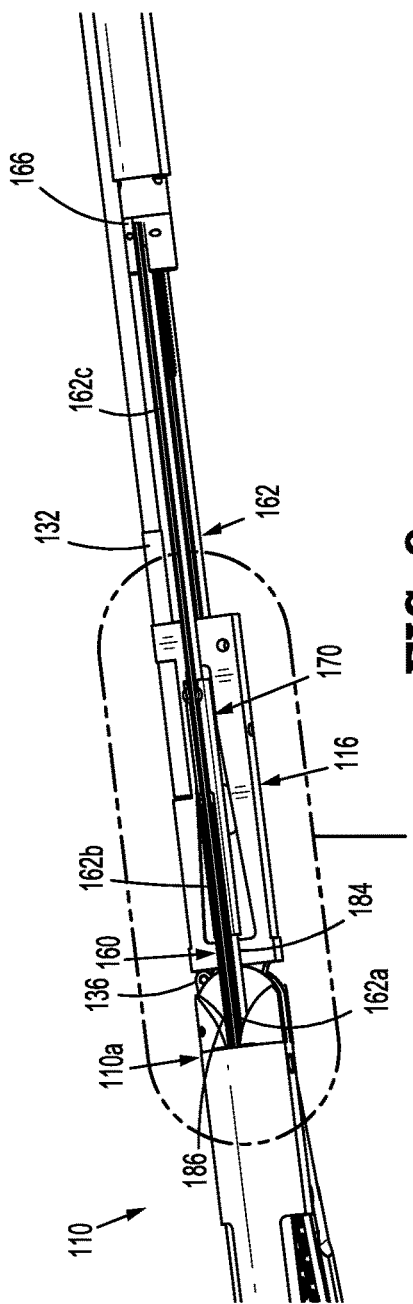
FIG. 8 is a top, perspective view, with the inner and outer housings of the elongate body removed, of the surgical loading unit of FIG. 7 further illustrating the knife assembly.

With reference to FIGS. 2A-2D, the end effector 110 of the loading unit 100 defines a second longitudinal axis "X2" that is aligned with the first longitudinal axis "X1" of the elongate body 102 when the end effector 110 is in a non-articulated position (FIGS. 2A-2D and 6A), and is misaligned with the first longitudinal axis "X1" of the elongate body 102 when the end effector 110 is in an articulated position (FIGS. 6B and 6C). The end effector 110 has a proximal portion 110a pivotably coupled to the distal portion 102b of the elongate body 102.

Figure 3:
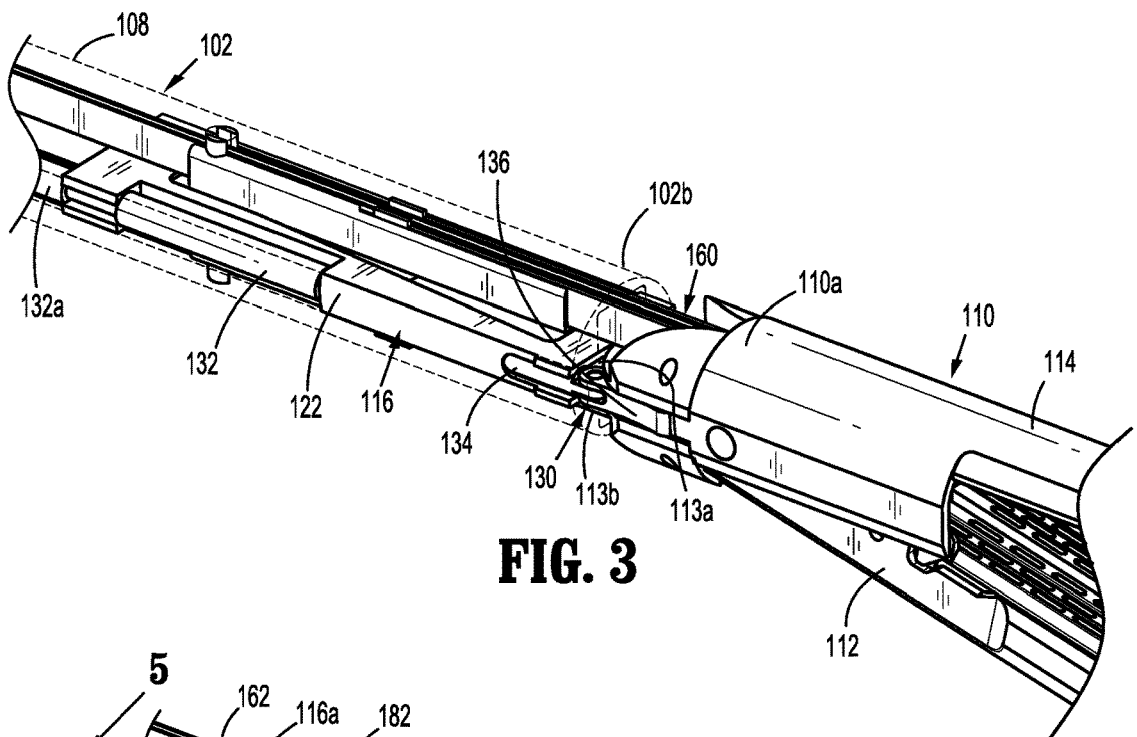
FIG. 3 is a perspective view, with an outer housing removed, of the loading unit of FIG. 2A illustrating an articulation mechanism and a knife assembly thereof.
Figure 4:
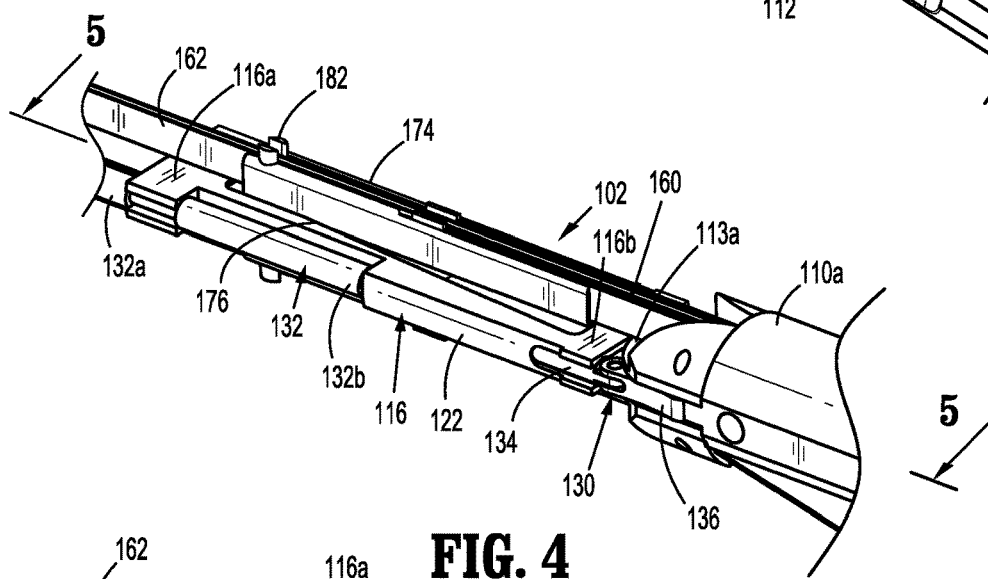
FIG. 4 is an enlarged view, with the outer housing and an inner housing removed, of the surgical loading unit of FIG. 3.
Figure 5:
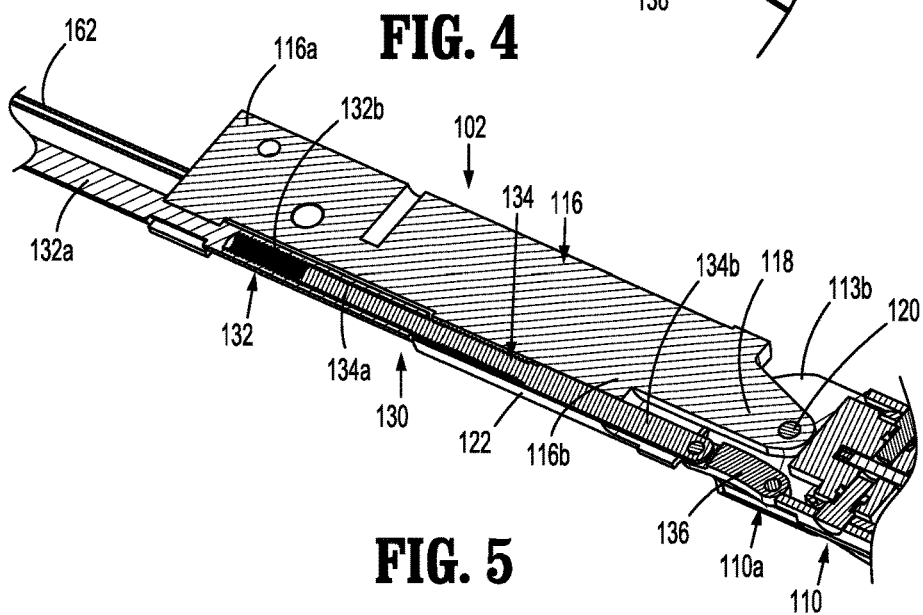
FIG. 5 is a perspective cross-sectional view, taken along line 5-5 in FIG. 4, of the loading unit illustrating the articulation mechanism.

In particular, with reference to FIGS. 3-6C, the distal portion 102b of the elongate body 102 of the loading unit 100 includes a support structure or platform 116 axially fixed within the inner housing 108 of the elongate body 102 (FIG. 3). The support structure 116 has an elongated, planar configuration, but in some embodiments, may assume any suitable configuration, such as tubular, cylindrical, or the like. The support structure 116 of the elongate body 102 has a distally-extending tapered extension 118. The proximal portion 110a of the end effector 110 includes a pair of flanges 113a, 113b extending proximally therefrom. The tapered extension 118 of the support structure 116 is received in the space defined between the pair of flanges 113a, 113b of the end effector 110. A pivot pin 120 extends through each of the tapered extension 118 of the support structure 116 of the elongate body 102 and the pair of flanges 113a, 113b of the end effector 110 to pivotably connect the end effector 110 to the elongate body 102. In some embodiments, other pivotable connections between the end effector 110 and the elongate body 102 are contemplated, such as, for example, a ball and socket connection.

With continued reference to FIGS. 3-6C, loading unit 100 includes an articulation assembly 130 that operably interconnects the end effector 110 to the elongate body 102 to facilitate articulation of the end effector 110 relative to the elongate body 102. The presently disclosed articulation assembly 130 is most suitable for use with the powered surgical stapling instrument 10b of FIG. 1B. However, it is contemplated that the articulation assembly 130 may be modified for use with the manually-operated surgical stapling instrument 10a of FIG. 1A.

The articulation assembly 130 of the loading unit 100 is laterally offset from a central longitudinal axis "X1" defined by the elongate body 102 and includes an elongated drive nut 132, an elongated drive screw 134 operably coupled to the drive nut 132, and an articulation link 136 operably coupled to the drive screw 134. The drive nut 132 and the drive screw 134 are axially aligned with one another and each extends parallel and laterally offset from the central longitudinal axis "X1" of the elongate body 102. The drive nut 132 extends through a proximal portion 116a of a longitudinal side 122 of the support structure 116, and the drive screw 134 extends through a distal portion 116b of the longitudinal side 122 of the support structure 116. The drive nut 132 is rotatably supported and axially fixed in the longitudinal side 122 of the support structure 116, and the drive screw 134 is keyed to the longitudinal side 122 of the support structure 116 to prevent rotation of the drive screw 134 while permitting linear translation of the drive screw 134 relative to the support structure 116.

By positioning the drive nut 132 and the drive screw 134 of the articulation assembly 130 adjacent the distal end of the elongate body 102 of the loading unit 100 rather than the proximal end, the amount of clearance build up that would ordinarily occur in the proximal end of the elongate body 102 is reduced.

The drive nut 132 of the articulation assembly 130 has a proximal portion 132a operably coupled to the actuation button 22 (FIG. 1B) of the handle assembly 20, and a distal portion 132b. The drive screw 134 of the articulation assembly 130 has a proximal portion 134a disposed within the distal portion 132b of the drive nut 132 and defines external threading operably coupled to internal threading defined in the drive unit 132. As such, rotation of the drive nut 132 relative to and within the support structure 116, in response to an actuation of the button 22 (FIG. 1B), effects linear translation of the drive screw 134 within and relative to the support structure 116.

The articulation link 136 of the articulation assembly 130 has a proximal portion 136a pivotably coupled to the distal portion 134b of the drive screw 134, and a distal portion 136b pivotably coupled to the proximal portion 110a (e.g., one or both of the flanges 113a or 113b) of the end effector 110. The articulation link 136 may have an arcuate configuration, with a convex lateral side oriented toward the pivot axis of the loading unit 100 and a concave side oriented away from the pivot axis. In some embodiments, the articulation link 136 may assume any suitable shape, such as, for example, linear. The articulation link 136 transfers the linear motion of the drive screw 134 into a pivoting motion to articulate the end effector 110 relative to the elongate body 102.

With reference to FIGS. 6A-6C, in use, rotation of the drive nut 132 of the articulation assembly 130 via an actuation of the button 22 (FIG. 1B) linearly translates the drive screw 134 of the articulation assembly 130 in one of a proximal or distal direction based on the direction of rotation of the drive nut 132. For example, as shown in FIG. 6B, a clockwise rotation of the drive nut 132 may result in a distal translation of the drive screw 134 relative to the drive nut 132. As the drive screw 134 translates in a distal direction, indicated by arrow "A" in FIG. 6B, the articulation link 136 of the articulation assembly 130 pivots about the proximal portion 136a thereof and relative to the distal portion 134b of the drive screw 134 in a first direction, indicated by arrow "B" in FIG. 6B, due to the end effector 110 being axially fixed relative to the elongate body 102. The articulation link 136 also pivots about the distal portion 136b thereof relative to the proximal portion 110a of the end effector 110, which effects articulation of the end effector 110 in the direction "B."

Similarly, as shown in FIG. 6C, counter-clockwise rotation of the drive nut 132 may result in a proximal translation of the drive screw 134 relative to the drive nut 132. As the drive screw 134 translates in a proximal direction, indicated by arrow "C" in FIG. 6C, the articulation link 136 pivots slightly about the proximal portion 136a thereof relative to the distal portion 134b of the drive screw 134. Since the distal portion 136b of the articulation link 136 is coupled to the end effector 110 at a location offset from the central longitudinal axis "X2" of the end effector 110, the end effector 110 articulates relative to the elongate body 102 in a direction indicated by arrow "D" in FIG. 6C.

With reference to FIGS. 2A-2D, 3, 4, and 7-12, the knife assembly 160 of the loading unit 100 is illustrated. As briefly mentioned above, the knife assembly 160 includes a flexible knife bar 162 that supports a knife blade 164 (FIG. 13B) at a first or distal segment 162a thereof and bends during the above-described articulation of the end effector 110 relative to the elongate body 102.

With specific reference to FIGS. 7-12, the knife bar 162 of the knife assembly 160 has a second or intermediate segment 162b extending through the elongate body 102 of the loading unit 100, and a third or proximal segment 162c operably coupled to a knife bar pusher 166 to couple the knife bar 162 to the button 22 (FIG. 1B) of the handle assembly 20, or to another actuation button of the handle assembly 20, e.g., an actuation button 23. The knife blade 164 (FIG. 13B) is coupled to or monolithically formed with the distal segment 162a of the knife bar 162. As such, an actuation of the button 23 distally translates the knife bar 162 and the associated knife blade 164 through the end effector 110 to cut tissue grasped by the end effector 110. The knife bar 162 is bifurcated along its length to define a pair of longitudinally-extending knife bar shafts 168a, 168b (FIG. 12) having the support structure 116 of the elongate body 102 disposed therebetween.

The knife assembly 160 further includes an elongate guide member or track 170 that supports the intermediate or second segment 162b of the knife bar 162. The track 170 is supported on a top side 117a of the support structure 116 and in the inner housing 108 (FIG. 3) of the elongate body 102 of the loading unit 100. The track 170 of the knife assembly 160 has a linear, rectangular shape and defines a longitudinally-extending channel 172 having the intermediate segment 162b of the knife bar 162 slidably supported therein. In embodiments, the track 170 may assume a variety of suitable shapes, such as, for example, tubular.

The track 170 includes a bottom wall 172 on which the intermediate segment 162b of the knife bar 162 is supported, and a pair of parallel side walls 174, 176 extending perpendicularly from the bottom wall 172. The pair of side walls 174, 176 extend along and support respective lateral sides 178a, 178b of the intermediate segment 162b of the knife bar 162 such that the track 170 at least partially surrounds the intermediate segment 162b of the knife bar 162. The track 170 is fabricated from a material that gives the track 170 axial stiffness, such as polyamide-imide or polyether ether ketone. The track 170 has a greater stiffness (e.g., less flexibility) than the flexible knife bar 162. Due to the track 170 having a greater axial stiffness than the knife bar 162, the track 170 resists bending along its length during articulation of the end effector 110 to maintain the linearity of the intermediate segment 162b of the knife bar 162.

The track 170 of the knife assembly 160 is movably supported on the top side 117a of the support structure 116 of the elongate body 102. The top side 117a of the support structure 116 defines a shallow cavity 180 therein. The track 170 is pivotably supported in the cavity 180 of the support structure 116. The cavity 180 defined in the support structure 116 has a proximal portion 180a and a distally-flaring distal portion 180b. The distal portion 180b of the cavity 180 allows for a distal portion 170b of the track 170 to traverse therein during articulation of the end effector 110, as will be described in detail below. The cavity 180 of the support structure 116 and the track 170 have substantially similar lengths such that the track 170 is prevented from longitudinal translation within the cavity 180 and relative to the support structure 116. In some embodiments, the track 170 may have a circular tab 182 extending from the parallel side walls 174, 176 of the track 170 that pivotably couples to the inner housing 108 (FIG. 3) of the elongate body 102 to allow for rotation of the track 170 relative to the support structure 116, but prevents longitudinal translation of the track 170 relative to the support structure 116.

With continued reference to FIGS. 7-12, the knife assembly 160 further includes blow-out plates or supports 184, 186 that extend along the lateral sides 178a, 178b of the knife bar 162, respectively. The blow-out plates 184, 186 are more flexible than the track 170 to allow bending of the plates 184, 186 during articulation of the end effector 110, but are less flexible than the knife bar 162 to prevent buckling of the distal segment 162a of the knife bar 162 during articulation of the end effector 110.

Each of the blow-out plates 184, 186 has a proximal portion 184a, 186a and a distal portion 184b, 186b, respectively. The proximal portion 184a of the first blow-out plate 184 is disposed between the first lateral side 178a of the knife bar 162 and the first side wall 174 of the track 170. The proximal portion 186a of the second blow-out plate 186 is disposed between the second lateral side 178b of the knife bar 162 and the second side wall 176 of the track 170. The proximal portion 184a, 186a of each of the blow-out plates 184, 186 are slidably received within the channel 172 of the track 170.

The distal portion 184b, 186b of each of the blow-out plates 184, 186 is fixed to the proximal portion 110a of the end effector 110. In this way, as the end effector 110 articulates relative to the elongate body 102, one of the blow-out plates 184 or 186 will be pulled in a proximal direction and the other of the blow-out plates 184 or 186 will be pushed in a distal direction due to changes in radial distance between the blow-out plates 184, 186 during articulation of the end effector 110. During the pushing and/or pulling of the distal portions 184b, 186b of the blow-out plates 184, 186, the proximal portions 184a, 186a thereof slide within and relative to the channel 172 of the track 170 and the knife bar 162.

Figure 12:
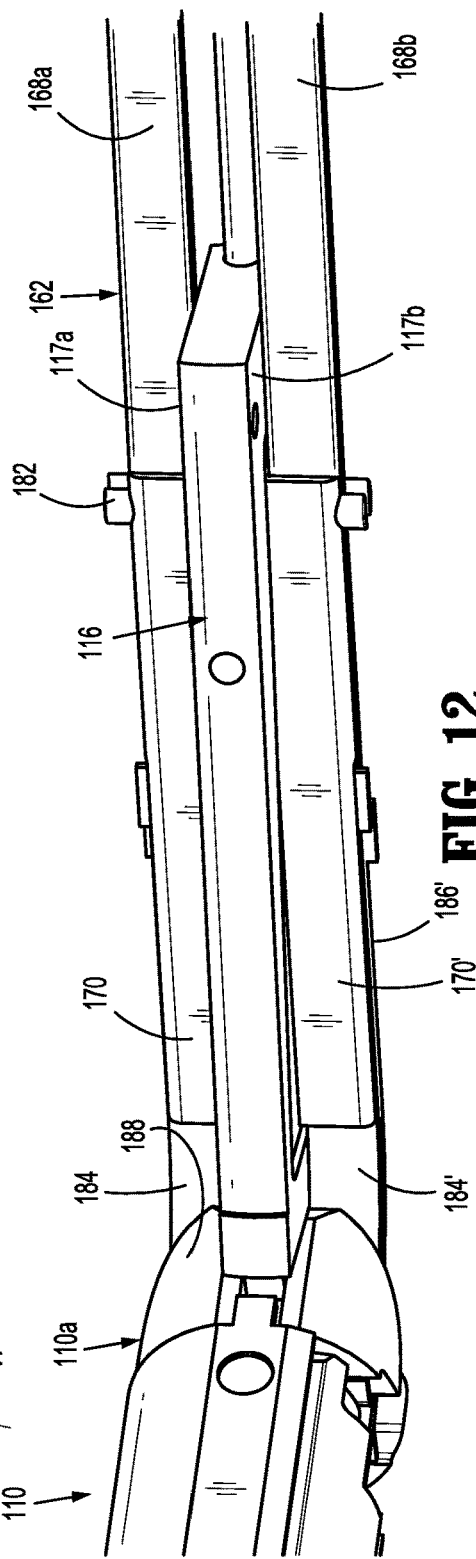
FIG. 12 is a side view of the surgical loading unit of FIG. 11 illustrating the end effector in the articulated position.

As shown in FIG. 12, the knife assembly 160 has another track 170' that supports the second knife bar shaft 168b of the knife bar 162 and another pair of blow-out plates 184', 186', each of which are disposed on the bottom side 117b of the support structure 116. Due to the substantial similarity of the components of the knife assembly 160 disposed on the top side 117a of the support structure 116 and the components of the knife assembly 160 disposed on the bottom side 117b of the support structure 116, the components of the knife assembly 160 on the bottom side 117b of the support structure 116 will not be described.

With continued reference to FIGS. 7-12, the proximal portion 110a of the end effector 110 of the loading unit 100 cooperates with the knife assembly 160 to facilitate bending of the knife bar 162 of the knife assembly 160 along its axis and a shifting of the knife bar 162 relative to the support structure 116 of the elongate body 102. The proximal portion 110a of the end effector 110 includes first and second walls 188, 190 that taper in a proximal direction. The walls 188, 190 of the end effector 110 are supported on the top flange 113a of the end effector 110. As described above, the knife bar 162 is divided into two shafts 168a, 168b, thus the proximal portion 110a of the end effector 110 may have another pair of walls (not explicitly shown) supported on the bottom flange 113b of the end effector 110 for interacting with the second knife bar shaft 168b of the knife bar 162. The first and second walls 188, 190 cooperatively define a proximally-flaring cavity 192 through which both the distal segment 162a of the knife bar 162 and the distal portion 184b, 186b of each of the blow-out plates 184, 186 extend. The cavity 192 of the proximal portion 110a of the end effector 110 accommodates movement of the distal segment 162a of the knife bar 162 as the knife bar 162 bends with articulation of the end effector 110 in either of the first or second directions.

Each of the first and second walls 188, 190 of the end effector 110 defines an arcuate side surface 194, 196, respectively. The arcuate side surfaces 194, 196 are laterally spaced from one another across the cavity 192 of the proximal portion 110a of the end effector 110. In some embodiments, the side surfaces 194, 196 of the first and second walls 188, 190 may assume a variety of shapes. The arcuate side surface 194 of the first wall 188 is oriented toward the first lateral side 178a of the knife bar 162, and the arcuate side surface 196 of the second wall 190 is oriented toward the second lateral side 178b of the knife bar 162. As will be described in detail below, during articulation of the end effector 110 relative to the elongate body 102, the arcuate side surfaces 194, 196 of the respective first and second walls 188, 190 of the end effector 110 contact the respective blow-out plates 184, 186 to bend the blow-out plates 184, 186 and the distal segment 162*a* of the knife bar 162.

Figure 11:
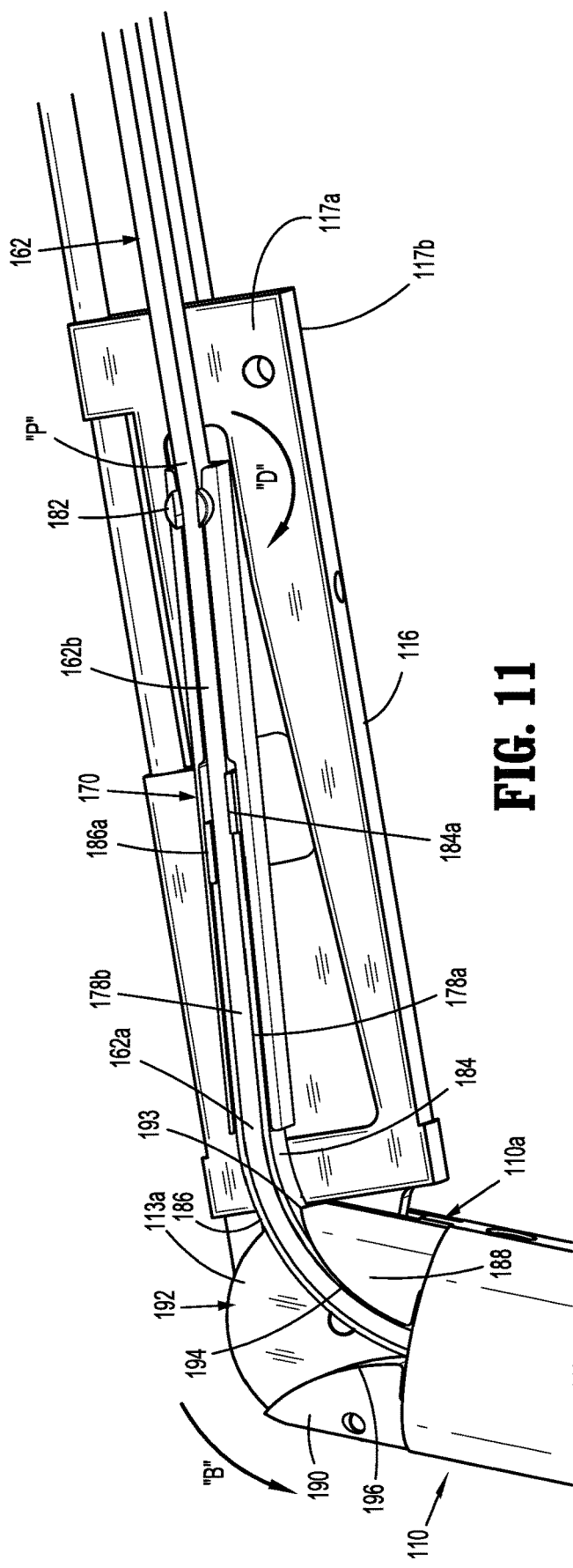
FIG. 11 is a top, perspective view, with parts removed, of the surgical loading unit of FIG. 9 illustrating the end effector in an articulated position.

In operation, the end effector 110 may be articulated relative to the elongate body 102 in either the first direction, as indicated by arrow "B" in FIGS. 6B and 11, or the second direction, as indicated by arrow "D" in FIG. 6C, via the articulation assembly 130 as described above. During articulation of the end effector 110 of the loading unit 100 in the first direction "B" relative to the elongate body 102, the distal segment 162*a* of the knife bar 162 (e.g., the segment of the knife bar 162 that spans each of the distal portion 102*b* of the elongate body 102 and the proximal portion 110*a* of the end effector 110) bends in the first direction "B."

Upon the end effector 110 achieving a threshold amount of articulation, the arcuate side surface 194 of the first wall 188 of the end effector 110 contacts the first blow-out plate 184 to urge the distal and intermediate segments 162*a*, 162*b* of the knife bar 162 in a substantially opposite direction as the first direction "B" (e.g., the direction indicated by arrow "D" in FIG. 11). Further articulation of the end effector 110 in the direction "B" results in a proximal end 193 of the first wall 188 of the end effector 110 to contact the first blow-out plate 184 to further urge the distal and intermediate segments 162*a*, 162*b* of the knife bar 162 in a substantially opposite direction from the motion of articulation of the end effector 110.

Since the second or intermediate segment 162*b* of the knife bar 162 is disposed within the channel 172 of the track 170 of the knife assembly 160, movement or shifting of the knife bar 162 in the direction "D" also causes the track 170 to move or shift in the direction "D." Due to the proximal portion 170*a* of the track 170 being axially fixed relative to the support structure 116, and the distal portion 170*b* of the track 170 being free to move, the distal portion 170*b* of the track 170 pivots about the proximal portion 170*a* thereof.

While the distal segment 162*a* of the knife bar 162 is curved during articulation of the end effector 110, the intermediate segment 162*b* of the knife bar 162 remains linear because the intermediate segment 162*b* of the knife bar 162 extends within the track 170. As the track 170 of the knife assembly 160 pivots in the direction "D," the distal portion 170*b* of the track 170 moves toward a first side of the central longitudinal axis "X1" defined by the elongate body 102 and a distal portion 110*b* (FIG. 2B) of the end effector 110 moves toward a second side of the central longitudinal axis "X1" defined by the elongate body 102.

As the track 170 of the knife assembly 160 pivots about the proximal portion 170*a* thereof, the knife bar 162 of the knife assembly 160 bends at a point "P" immediately proximal the proximal portion 170*a* of the track 170 given the knife bar 162 is disposed outside of the track 170 at the point "P." While the distal segment 162*a* of the knife bar 162 is being bent in the direction "B" during articulation of the end effector 110, the knife bar 162 at the point "P" bends in the direction "D." In this way, the distal and intermediate segments 162*a*, 162*b* of the knife bar 162 are shifting or pivoting in an opposite direction from the direction the distal segment 162*a* of the knife bar 162 is bending or curving. By moving the distal and intermediate segments 162*a*, 162*b* of the knife bar 162 in a direction opposite from that of the bending direction of the distal segment 162*a* of the knife bar 162, the radius of curvature of the distal segment 162*a* of the knife bar 162 is increased. Increasing the radius of curvature of the distal segment 162*a* of the knife bar 162 reduces stresses on the knife bar 162 during articulation of the end effector 110 in the direction "B."

Articulation of the end effector 110 of the loading unit 100 in the opposite direction (e.g., direction "D") causes a similar phenomenon in the knife bar 162 of the knife assembly 160, but in the opposite directions. In particular, as the end effector 110 is articulated in the second direction "D," the distal segment 162*a* of the knife bar 162 is bent or curved in the second direction "D." Upon the end effector 110 achieving a threshold amount of articulation, the arcuate side surface 196 of the second wall 190 of the end effector 110 contacts the second blow-out plate 186 of the knife assembly 160 to urge the distal and intermediate segments 162*a*, 162*b* of the knife bar 162 in a substantially opposite direction as the second direction "D" (e.g., direction "B".)

Since the intermediate segment 162*b* of the knife bar 162 is disposed within the channel 172 of the track 170, movement or shifting of the intermediate segment 162*b* of the knife bar 162 in the direction "B" also causes the track 170 to move or pivot in the direction "B." As the track 170 pivots about the proximal portion 170*a* thereof, the knife bar 162 bends at the point "P." The linear profile of the intermediate segment 162*b* of the knife bar 162 is maintained by the track 170 while the knife bar 162 at the point "P" bends in the direction "B." In this way, the distal segment 162*a* of the knife bar 162 is being bent or curved in an opposite direction from the direction the distal and intermediate segments 162*a*, 162*b* of the knife bar 162 are shifting or moving. By moving the distal and intermediate segments 162*a*, 162*b* of the knife bar 162 in an opposite direction from that of the bending direction of the distal segment 162*a* of the knife bar 162, the radius of curvature of the distal segment 162*a* of the knife bar 162 is increased. Increasing the radius of curvature of the distal segment 162*a* of the knife bar 162 reduce stresses on the knife bar 162 during articulation of the end effector 110 in the direction "D."

Figure 13A:
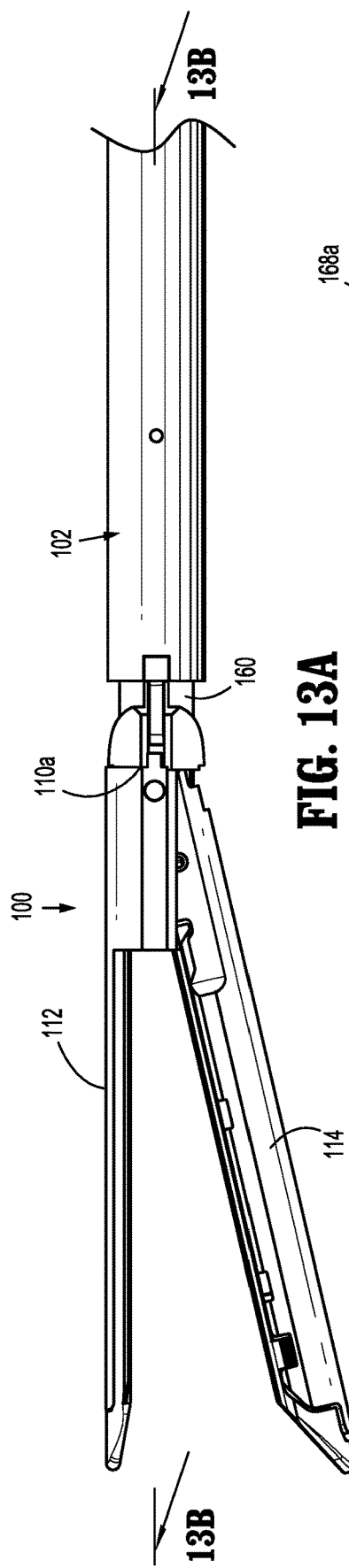
FIG. 13A is a side view of the surgical loading unit illustrating a staple cartridge and an anvil of the end effector in an open position.
Figure 13B:
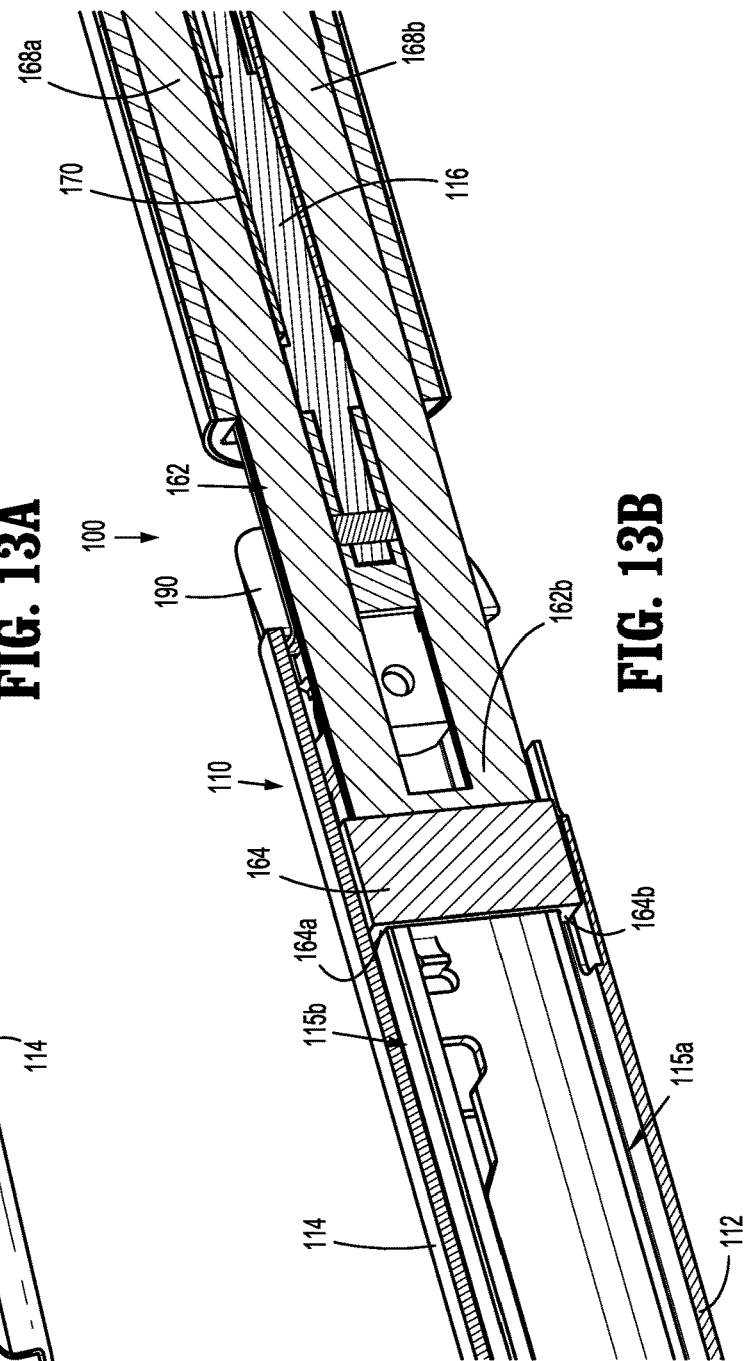
FIG. 13B is a cross-section, taken along line 13B-13B, of the end effector of FIG. 13A, illustrating the staple cartridge and the anvil in an approximated configuration.

With reference to FIGS. 13 and 14, the staple cartridge 112 and the anvil 114 of the end effector 110 are illustrated. Each of the staple cartridge 112 and the anvil 114 define longitudinally-extending channels 115*a*, 115*b*, respectively. A top portion of the knife blade 164 has a laterally-extending projection 164*a* slidably captured within the channel 115*b* of the anvil 114, and a bottom portion of the knife blade 164 has a laterally-extending projection 164*b* slidably captured within the channel 115*a* of the staple cartridge 112. The channels 115*a*, 115*b* support the knife blade 164 therein to stabilize the knife blade 164 during translation of the knife blade 164 through the end effector 110.

The present disclosure also relates to methods of using the described surgical stapling instruments 10*a*, 10*b* to perform a surgical procedure and/or to articulate an end effector of a surgical stapling loading unit. Staples may be fired from the staple cartridge of the end effector employing a similar mechanism disclosed in U.S. Pat. No. 6,953,139 to Milliman et al., which has been incorporated by reference herein.

Persons skilled in the art will understand that the loading units and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A surgical loading unit comprising:
an elongate body;
an end effector having a proximal portion pivotably coupled to a distal portion of the elongate body; and
a flexible knife bar extending through the distal portion of the elongate body, the flexible knife bar having a first segment and a second segment, wherein the first segment of the flexible knife bar is configured to curve in a first direction in response to an articulation of the end effector relative to the elongate body in the first direction, and the second segment of the flexible knife bar is configured to pivot in a second direction, opposite the first direction, in response to the articulation of the end effector relative to the elongate body in the first direction.

2. The surgical loading unit according to claim 1, wherein the second segment is disposed proximally of the first segment.

3. The surgical loading unit according to claim 1, wherein the second segment is configured to resist deformation as the second segment pivots in the second direction.

4. The surgical loading unit according to claim 1, further comprising an elongate guide member pivotably supported in the distal portion of the elongate body and defining a longitudinally-extending channel, wherein the flexible knife bar is received in the channel of the elongate guide member.

5. The surgical loading unit according to claim 4, wherein the second segment is slidably received in the channel of the elongate guide member.

6. The surgical loading unit according to claim 4, wherein articulation of the end effector relative to the elongate body in the first direction effects movement of a distal portion of the elongate guide member in the second direction.

7. The surgical loading unit according to claim 6, wherein the proximal portion of the end effector includes:
a first wall that tapers proximally; and
a second wall that tapers proximally such that the first and second walls cooperatively define a proximally-flaring cavity through which the first segment of the flexible knife bar extends.

8. The surgical loading unit according to claim 7, wherein each of the first and second walls defines an arcuate side surface, the arcuate side surfaces being laterally spaced from one another.

9. The surgical loading unit according to claim 7, wherein the first wall has a proximal portion configured to engage the flexible knife bar in response to the articulation of the end effector in the first direction to move the distal portion of the elongate guide member in the second direction, and the second wall has a proximal portion configured to engage the flexible knife bar in response to an articulation of the end effector in the second direction to move the distal portion of the elongate guide member in the first direction.

10. The surgical loading unit according to claim 4, wherein the elongate guide member includes a proximal portion pivotably coupled to the elongate body, such that the elongate guide member is prevented from translating longitudinally relative to the elongate body.

11. The surgical loading unit according to claim 4, further comprising another elongate guide member defining a longitudinally-extending channel, the flexible knife bar including:
a first knife bar shaft extending through the channel of the elongate guide member; and
a second knife bar shaft coupled to and extending parallel with the first knife bar shaft, the second knife bar shaft extending through the channel of the another elongate guide member.

12. The surgical loading unit according to claim 11, further comprising a support structure disposed between the first and second knife bar shafts of the flexible knife bar, the support structure including:
a top surface on which the elongate guide member is supported; and
a bottom surface on which the another elongate guide member is supported.

13. The surgical loading unit according to claim 1, further comprising a pair of blow-out plates extending along opposite sides of the flexible knife bar, wherein in response to the end effector articulating, the first blow-out plate is configured to slide relative to the elongate guide member in a first axial direction and the second blow-out plate is configured to slide relative to the elongate guide member in a second axial direction.

14. The surgical loading unit according to claim 1, further comprising an articulation assembly for effecting articulation of the end effector, the articulation assembly including:
an elongated drive nut disposed in the distal portion of the elongate body;
an elongated drive screw disposed in the distal portion of the elongate body and threadingly coupled to the drive nut; and
an articulation link having a proximal portion pivotably coupled to a distal portion of the drive screw or the drive nut, and a distal portion pivotably coupled to the proximal portion of the end effector.

15. A surgical instrument, comprising:
an elongate body;
an end effector having a proximal portion pivotably coupled to a distal portion of the elongate body;
an elongate guide member pivotably supported in the distal portion of the elongate body and defining a longitudinally-extending channel; and
a flexible knife bar extending through the channel of the elongate guide member, the knife bar configured to move through the channel of the elongate guide member, wherein the flexible knife bar has a distal segment and a proximal segment, wherein the distal segment of the flexible knife bar is configured to curve in a first direction in response to an articulation of the end effector relative to the elongate body in the first direction, and the proximal segment of the flexible knife bar is configured to pivot in a second direction, opposite the first direction, in response to the articulation of the end effector relative to the elongate body in the first direction.

16. The surgical instrument according to claim 15, wherein the elongate guide member has a distal portion, and wherein articulation of the end effector relative to the elongate body in the first direction effects movement of the distal portion of the elongate guide member in the second direction.

17. The surgical instrument according to claim 15, wherein the proximal segment of the flexible knife bar is slidably received in the channel of the elongate guide member, the elongate guide member being configured to resist deformation of the proximal segment of the flexible knife bar as the proximal segment of the flexible knife bar pivots.

18. The surgical instrument according to claim 15, further comprising:
- another elongated guide member defining a longitudinally-extending channel, the flexible knife bar including a first knife bar shaft extending through the channel of the elongate guide member, and a second knife bar shaft coupled to and extending parallel with the first knife bar shaft, the second knife bar shaft extending through the channel of the another elongate guide member; and
- a support structure disposed between the first and second knife bar shafts of the flexible knife bar, the support structure including:
  - a top surface on which the elongate guide member is supported; and
  - a bottom surface on which the another elongate guide member is supported.

19. The surgical instrument according to claim 15, further comprising an articulation assembly for effecting articulation of the end effector, the articulation assembly including:
- an elongated drive nut disposed in the distal portion of the elongate body;
- an elongated drive screw disposed in the distal portion of the elongate body and threadingly coupled to the drive nut; and
- an articulation link having a proximal portion pivotably coupled to a distal portion of the drive screw or the drive nut, and a distal portion pivotably coupled to the proximal portion of the end effector.

20. A surgical instrument, comprising:
- an elongate body;
- an end effector having a proximal portion pivotably coupled to a distal portion of the elongate body;
- an elongate guide member pivotably supported in the distal portion of the elongate body and defining a longitudinally-extending channel;
- a flexible knife bar extending through the channel of the elongate guide member, the knife bar configured to move through the channel of the elongate guide member; and
- an articulation assembly for effecting articulation of the end effector, the articulation assembly including:
  - an elongated drive nut disposed in the distal portion of the elongate body;
  - an elongated drive screw disposed in the distal portion of the elongate body and threadingly coupled to the drive nut; and
  - an articulation link having a proximal portion pivotably coupled to a distal portion of the drive screw or the drive nut, and a distal portion pivotably coupled to the proximal portion of the end effector.

\* \* \* \* \*